(12) United States Patent
Rolland et al.

(10) Patent No.: US 7,700,351 B2
(45) Date of Patent: *Apr. 20, 2010

(54) METHODS AND COMPOSITIONS FOR TISSUE REGENERATION

(75) Inventors: Eric Rolland, Divonne les bains (FR);
Thomas Hunziker, Oberhofen (CH);
Beatrice Mis, Lausanne (CH);
Christopher Rinsch, Lausanne (CH)

(73) Assignee: DFB Pharmaceuticals, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/255,481

(22) Filed: Oct. 21, 2008

(65) Prior Publication Data

US 2009/0232791 A1 Sep. 17, 2009

Related U.S. Application Data

(63) Continuation of application No. 10/526,853, filed as application No. PCT/US03/027888 on Sep. 5, 2003, now Pat. No. 7,449,333, which is a continuation of application No. 10/324,257, filed on Dec. 19, 2002, now Pat. No. 7,144,729.

(60) Provisional application No. 60/408,565, filed on Sep. 6, 2002.

(51) Int. Cl.
*C12N 5/00* (2006.01)
*C12N 5/02* (2006.01)
*C12N 5/08* (2006.01)

(52) U.S. Cl. .................. 435/325; 435/366; 435/371; 604/890.1; 424/93.1

(58) Field of Classification Search .................. None
See application file for complete search history.

(56) References Cited

U.S. PATENT DOCUMENTS

| | | | | |
|---|---|---|---|---|
| 4,837,379 | A | 6/1989 | Weinberg | 424/548 |
| 5,261,255 | A * | 11/1993 | Coelho et al. | 62/376 |
| 5,290,552 | A | 3/1994 | Sierra et al. | 424/94.64 |
| 5,855,617 | A | 1/1999 | Orton | 623/11 |
| 5,863,296 | A | 1/1999 | Orton | 623/15 |
| 5,891,558 | A | 4/1999 | Bell et al. | 428/218 |
| 5,902,608 | A | 5/1999 | Read et al. | 424/532 |
| 5,948,429 | A | 9/1999 | Bell et al. | 424/426 |
| 5,968,546 | A | 10/1999 | Baur et al. | 424/444 |
| 6,010,887 | A | 1/2000 | Bridges et al. | 435/91.1 |
| 6,054,122 | A | 4/2000 | MacPhee et al. | 424/94.4 |
| 6,479,052 | B1 | 11/2002 | Marshall et al. | 424/93.7 |
| 6,503,539 | B2 | 1/2003 | Gestrelius et al. | 514/2 |
| 6,692,738 | B2 | 2/2004 | MacLaughlin et al. | 424/93.21 |
| 6,720,009 | B2 | 4/2004 | Gestrelius et al. | 514/2 |
| 6,730,313 | B2 * | 5/2004 | Helmus et al. | 424/423 |
| 2003/0166274 | A1 | 9/2003 | Hewitt et al. | 435/6 |

FOREIGN PATENT DOCUMENTS

| | | |
|---|---|---|
| DE | 19949290 | 4/2001 |
| EP | 0 339 607 | 11/1989 |
| ES | 2132027 | 8/1999 |
| JP | 2000-501299 | 2/2000 |
| JP | 2001-517431 | 10/2001 |
| WO | WO 97/06835 | 2/1997 |
| WO | WO 99/15637 | 4/1999 |
| WO | WO 00/25838 | 5/2000 |
| WO | WO 00/32207 | 6/2000 |
| WO | WO 01/24842 | 4/2001 |
| WO | WO 02/072800 | 9/2002 |
| WO | WO 02/078721 | 10/2002 |

OTHER PUBLICATIONS

Badiavas, et al., "Retrovirally Mediated Gene Transfer in a Skin Equivalent Model of Chronic Wounds", *J. Dermatol. Sci.*, 13:56-62, 1996.

Cooper, et al., "Use of a Composite Skin Graft Composed of Cultured Human Keratinocytes and Fibroblasts and a Collagen-GAG Matrix to Cover Full-Thickness Wounds on Athynic Mice", *Surgery*, 109:198-207, 1991.

Currie, et al., "The Use of Fibrin Glue in Skin Grafts and Tissue-Engineered Skin Replacements: A Review", *Plast. Reconstr. Surg.*, 108:1713-1726, 2001.

Database Prous Science Intergrity (Online), "Modex advances Alox through early-stage clinical testing," Database accession No. 323719, Aug. 7, 2002.

Database WPI, "Artificial skin production-comprises cell cultivation of keratinocytes on base of gel of human fibrin populated with human fibroblasts," Section Ch., Week 199940, Derwent Publications, Ltd., AN 1999-471189, 1999.

Davies, "Synthetic materials for covering burn wounds: progress towards perfection. Part I. Short term dressing materials," *Burns Incl Therm Inj.* 10:94-103, 1983.

(Continued)

*Primary Examiner*—Gary B Nickol
*Assistant Examiner*—Daniel C Gamett
(74) *Attorney, Agent, or Firm*—Fulbright & Jaworski L.L.P.

(57) ABSTRACT

Disclosed is a kit comprising a first component comprising fibrinogen, aprotinin, and a buffered solution, and a second component comprising, fibroblasts, keratinocytes, thrombin, glycerol, human serum albumin, and a buffered solution, wherein the first and second components are comprised in separate sterile containers.

10 Claims, 13 Drawing Sheets

OTHER PUBLICATIONS

Del Rio, I., "A Preclinical Model for the Analysis of Genetically Modified Human Skin In Vivo," *Human Gene Therapy*, 13:959-968, 2002.

Hunt et al., In: *Current Surgical Diagnosis & Treatment* pp. 86-98, 1988.

Hunt et al., In:. *The Surgical Wound*, Dineen & Hildrick-Smith, eds., pp. 1-18, 1981.

International Search Report issued in International Application No. PCT/US03127888, dated Dec. 4, 2003.

International Search Report issued in International Application No. PCT/USOI/27104, dated Apr. 8, 2002.

Kannon and Garrett, "Moist wound healing with occlusive dressings. A clinical review," *Dermatol. Surg.*, 21:583-590, 1995.

Kolodka et al., "Evidence for Keratinocyte Stem Cells in vitro: Long Tenn Engraftment and Persistence of Transgene Expression from Retrovirus-Transduced Kerationocytes," *Proc. Natl. Acad. Sci. USA*, 95:4356-4361, 1998.

Kuroyanagi et al., "A Cultured Skin Substitute Composed of castsand Kerationocytes with a Collagen Matrix: Preliminary Results of Clinical Trials," *Ann. Plait. Surg.*, 31:340-351, 1993.

Langdon et al., "Reconstruction of Structure and Cell Function in Human Skin Grafts Derived from Cryopreserved Allogenic and Autologous Cultured Keratinocytes," *J. Invest. Dermatol.*, 91:478-485, 1988.

Marugachi, et al., "A New Skin Equivalent: Kerationocytes Proliferated and Differentiated on Collagen Sponge Containing Fibroblasts," *Plast. Reconstr. Surg.*, 93:537-546, 1994.

Office Communication, issued in U.S. Appl. No. 10/324,527, dated Apr. 14, 2006.

Office Communication, issued in U.S. Appl. No. 10/324,527, dated Jul. 22, 2005.

Office Communication, issued in U.S. Appl. No. 10/324,527, dated Apr. 13, 2005.

Office Communication, issued in U.S. Appl. No. 10/526,853, dated Aug. 21, 2008.

Office Communication, issued in U.S. Appl. No. 10/526,853, dated Jan. 8, 2008.

Richey et al. "Topical growth factors and wound contraction in the rat: Part I. Literature review and definition of the rat model," *Annals of Plastic Surgery* 23(2): 159-165, 1989.

Riley, "Wound healing," *Am. Pam. Physician* 24: 107-113, 1981.

Singer et al., "Cutaneous Wound Healing," *New England Journal of Medicine*, 341:738-746, 1999.

Sugihara et al., "Effects of Fat Cells on Keratinocytes and Fibroblasts in a Reconstructed Rat Skin Model Using Collagen Gel Matrix Culture," *British J. Dennatol.*, 144:244-253, 2001.

Supplementary European Search Report issued in European Patent Application No. 03755791.5, dated Mar. 28, 2008.

Winter, "Formation of the scab and the rate of epithelization of superficial wounds in the skin of the young domestic pig," *Nature*, 193: 293.294, 1962.

Office Communication, issued in Japanese Patent Application No. 2003-157362, dated Oct. 15, 2009. (English Translation).

\* cited by examiner

Fig. 3

| | Fibrinogen 1/4 | Fibrinogen 1/8 | Fibrinogen 1/10 | Fibrinogen 1/20 | Fibrinogen 1/40 | Fibrinogen 1/80 | |
|---|---|---|---|---|---|---|---|
| Thrombin 1/4 | +++ | +++ | ++ | ++ | + | - | Strength |
| | +++ | +++ | ++ | ++ | ++ | + | Consistency |
| | 2 | 2 | 2 | 5 | 10 | 30 | Polymerization Time (sec) |
| Thrombin 1/8 | +++ | +++ | +++ | ++ | + | - | Strength |
| | +++ | +++ | +++ | ++ | ++ | + | Consistency |
| | 2 | 3 | 3 | 5 | 20 | 30 | Polymerization Time (sec) |
| Thrombin 1/10 | +++ | ++ | ++ | ++ | + | - | Strength |
| | +++ | +++ | +++ | ++ | + | - | Consistency |
| | 2 | 5 | 5 | 5 | 20 | 30 | Polymerization Time (sec) |
| Thrombin 1/20 | ++ | ++ | + | + | - | - | Strength |
| | ++ | ++ | ++ | + | - | - | Consistency |
| | 4 | 5 | 5 | 5 | 20 | 30 | Polymerization Time (sec) |
| Thrombin 1/40 | ++ | + | + | + | - | - | Strength |
| | ++ | + | + | + | - | - | Consistency |
| | 10 | 15 | 15 | 15 | 20 | 30 | Polymerization Time (sec) |
| Thrombin 1/80 | + | - | - | - | - | - | Strength |
| | ++ | ++ | + | + | - | - | Consistency |
| | 15 | 20 | 20 | 20 | 30 | 30 | Polymerization Time (sec) |

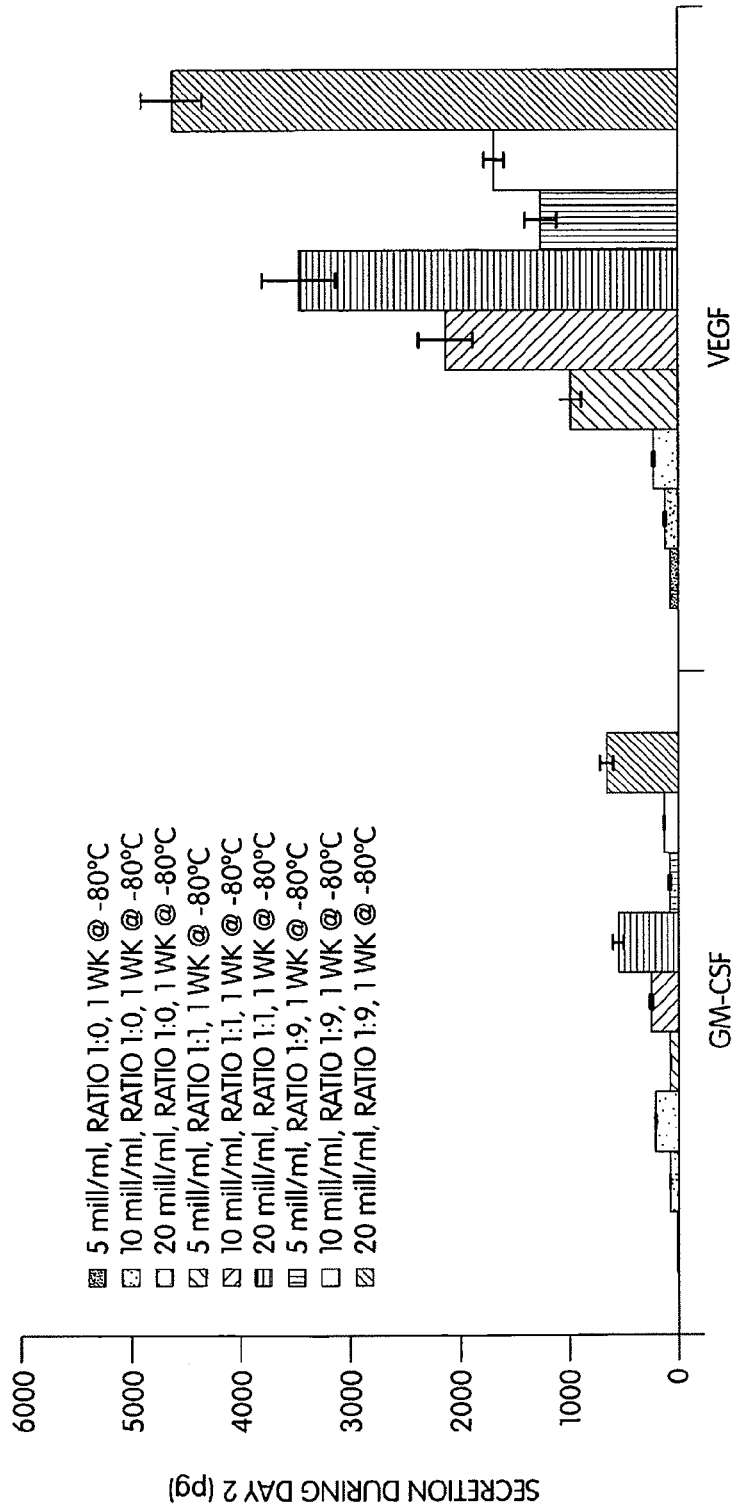

METHODS AND COMPOSITIONS FOR TISSUE REGENERATION

This application is a continuation of co-pending U.S. patent application Ser. No. 10/526,853 filed Jan. 9, 2006 now U.S. Pat. No. 7,449,333, which is a U.S. national phase application under 35 U.S.C. § 371 of PCT Application No. PCT/US2003/027888 filed on Sep. 5, 2003, which claims priority to U.S. patent application Ser. No. 10/324,257 filed on Dec. 19, 2002 (now issued as U.S. Pat. No. 7,144,729), which claims priority to U.S. Provisional Application No. 60/408,565 filed on Sep. 6, 2002. The contents of all of the above-referenced applications are incorporated by reference.

FIELD OF THE INVENTION

The present invention relates generally to tissue regeneration, e.g., the treatment of wounds using growth factor-, cytokine-, or angiogenic factor-secreting cells admixed with a biological or synthetic extracellular matrix and/or attached or applied to a wound dressing or solid nondegradable support matrix.

BACKGROUND OF THE INVENTION

Wounds (i.e., lacerations or openings) in mammalian tissue can result in tissue disruption and coagulation of the microvasculature at the wound face. Repair of such tissue represents an orderly, controlled cellular response to injury. All soft tissue wounds, regardless of size, heal in a similar manner. The mechanisms of tissue growth and repair are biologic systems wherein cellular proliferation and angiogenesis occur in the presence of an oxygen gradient. The sequential morphological and structural changes, which occur during tissue repair have been characterized in great detail and have, in some instances, been quantified. See Hunt, T. K., et al., "Coagulation and macrophage stimulation of angiogenesis and wound healing," in The surgical wound, pp. 1-18, ed. F. Dineen & G. Hildrick-Smith (Lea & Febiger, Philadelphia: 1981).

Tissue regeneration in various organs, such as, e.g., the skin or the heart depends on connective tissue restoring blood supply and enabling residual organ-specific cells such as keratinocytes or muscle cells to reestablish organ integrity. Thus, a relevant function of the mesenchymal cells, i.e., the fibroblasts or, in addition, the endothelial cells of vasculature, is secretion of factors enhancing the healing process, e.g., factors promoting formation of new blood vessels (angiogenesis) or factors promoting re-epithelialization by proliferating and migrating keratinocytes.

The cellular morphology of a wound consists of three distinct zones. The central avascular wound space is oxygen deficient, acidotic and hypercarbic, and has high lactate levels. Adjacent to the wound space is a gradient zone of local ischemia, which is populated by dividing fibroblasts. Behind the leading zone is an area of active collagen synthesis characterized by mature fibroblasts and numerous newly formed capillaries (i.e., neovascularization). While new blood vessel growth (angiogenesis) is necessary for the healing of wound tissue, angiogenic agents generally are unable to fulfill the long-felt need of providing the additional biosynthetic effects of tissue repair. Despite the need for more rapid healing of wounds (i.e., severe burns, surgical incisions, lacerations and other trauma), to date there has been only limited success in accelerating wound healing with pharmacological agents.

The primary goal in the treatment of wounds is to achieve wound closure. Open cutaneous wounds represent one major category of wounds. This category includes acute surgical and traumatic, e.g., chronic ulcers, burn wounds, as well as chronic wounds such as neuropathic ulcers, pressure sores, arterial and venous (stasis) or mixed arterio-venous ulcers, and diabetic ulcers. Open cutaneous wounds routinely heal by a process comprising six major components: i) inflammation, ii) fibroblast proliferation, iii) blood vessel proliferation, iv) connective tissue synthesis, v) epithelialization, and vi) wound contraction. Wound healing is impaired when these components, either individually or as a whole, do not function properly. Numerous factors can affect wound healing, including malnutrition, infection, pharmacological agents (e.g., cytotoxic drugs and corticosteroids), diabetes, and advanced age. See Hunt et al., in Current Surgical Diagnosis & Treatment (Way; Appleton & Lange), pp. 86-98 (1988).

Skin wounds that do not readily heal can cause the subject considerable physical, emotional, and social distress as well as great financial expense. See e.g. Richey et al., Annals of Plastic Surgery 23(2):159-65 (1989). Indeed, wounds that fail to heal properly finally may require more or less aggressive surgical treatment, e.g., autologous skin grafting. A number of treatment modalities have been developed as scientists' basic understanding of wounds and wound healing mechanisms has progressed.

The most commonly used conventional modality to assist in cutaneous wound healing involves the use of wound dressings. In the 1960s, a major breakthrough in wound care occurred when it was discovered that wound healing with a moist occlusive dressings was, generally speaking, more effective than the use of dry, non-occlusive dressings. See Winter, Nature 193:293-94 (1962). Today, numerous types of dressings are routinely used, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer). See Kannon et al., Dermatol. Surg. 21:583-590 (1995); Davies, Burns 10:94 (1983). Unfortunately, certain types of wounds (e.g., diabetic ulcers, pressure sores) and the wounds of certain subjects (e.g., recipients of exogenous corticosteroids) do not heal in a timely manner (or at all) with the use of such dressings.

Several pharmaceutical modalities have also been utilized in an attempt to improve wound healing. For example, treatment regimens involving zinc sulfate have been utilized by some practitioners. However, the efficacy of these regimens has been primarily attributed to their reversal of the effects of sub-normal serum zinc levels (e.g., decreased host resistance and altered intracellular bactericidal activity). See Riley, Am. Fam. Physician 24:107 (1981). While other vitamin and mineral deficiencies have also been associated with decreased wound healing (e.g., deficiencies of vitamins A, C and D; and calcium, magnesium, copper, and iron), there is no strong evidence that increasing the serum levels of these substances above their normal levels actually enhances wound healing. Thus, except in very limited circumstances, the promotion of wound healing with these agents has met with little success.

What is needed is a safe, effective, and interactive means for enhancing the healing of extensive and/or hard-to-heal wounds that can be used without regard to the type of wound or the nature of the patient population.

SUMMARY OF THE INVENTION

The present invention relates to the use of angiogenic or other growth factors or cytokines expressed by human cells in unencapsulated preparations (mixed or combined with matrix material or synthetic biocompatible substances) to be temporarily applied to wounds or defects in skin or other tissues for the restoration of blood supplying connective tissue to enable organ-specific cells to reestablish organ integrity as well as to inhibit excessive scar formation.

In one aspect, the invention involves a cell preparation useful for tissue regeneration, e.g., for use in the treatment of skin wounds, containing one or more cell types that secrete one or more biologically active substances, admixed with or applied to an extracellular matrix or matrix material such that the admixture forms a viscous or polymerized cell preparation. As used herein, the term "admixed" encompasses any methods of combining, mixing, blending, joining etc. known to those skilled in the art. The cell types used in the cell preparation of the invention are allogeneic, optionally mitotically inactivated, and selected from the group consisting of stromal, epithelial or organ specific, or blood-derived cells. For example, the cell types may be differentiated fibroblasts and keratinocytes. In other embodiments, the cell types may be selected from the group consisting of fibroblasts, keratinocytes (including outer root sheath cells), melanocytes, endothelial cells, pericytes, monocytes, lymphocytes (including plasma cells), thrombocytes, mast cells, adipocytes, muscle cells, hepatocytes, neurons, nerve or neuroglia cells, osteocytes, osteoblasts, corneal epithelial cells, chondrocytes, and/or adult or embryonic stem cells.

The main cell type of connective tissue is the fibroblast. Until recently, fibroblasts have been dealt with like homogenous non-differentiating cell populations. However, the fibroblast cell system in various species, including man, is a stem cell system in which the fibroblasts terminally differentiate along seven stages, three containing mitotic and four including post-mitotic cells. See Bayreuther et al., Proc. Natl. Acad. Sci. USA 85:5112-16 (1988); Bayreuther et al., J. Cell. Sci. Suppl. 10:115-30 (1988). In vitro induction of fibroblast differentiation may be performed by chemical or biological agents, such as mitomycin C (Brenneisen et al., Exp. Cell. Res. 211:219-30 (1994)) or growth factors or cytokines (Hakenjos et al., Int. J. Radiat. Biol. 76:503-09 (2000)) such as TGF beta 1, IL-1, IL-6, Interferon alpha. In vitro induction may also be accomplished by irradiation, e.g., with γ-rays; X-rays (Bumann et al., Strahlenther. Onkol. 171:35-41 (1995); UV light (Rodemann et al., Exp. Cell. Res. 180:84-93 (1989); or physical exposure to electromagnetic fields (Thumm et al., Radiat. Environ. Biophys. 38:195-99 (1999). Moreover, induction of differentiation may also be accomplished by culture conditions such as serum starvation, contact inhibition, or the addition of Mitomycin C. See Palka et al., Folia Histochem. Cytobiol. 34:121-27 (1996).

To date, the function/biological properties of differentiated fibroblasts have been poorly studied. The pattern of polypeptide expression and secretion, however, varies from mitotic to post-mitotic stages. The respective polypeptides are still being analyzed. See, e.g., Francz, Eur. J. Cell. Biol. 60:337-45 (1993).

In some embodiments, the biologically active molecule is at least one angiogenic factor, at least one growth/cytokine factor, or a combination of at least one angiogenic factor and at least one growth/cytokine factor. Examples of suitable biologically active molecules include, but are not limited to, epidermal growth factor-growth factor family (EGF); transforming growth factor alpha (TGF alpha); hepatocyte growth factor (HGF/SF); Heparin-binding epidermal growth factor (EGF); basic fibroblast growth factor (bFGF); acidic fibroblast growth factor (aFGF); other fibroblast growth factors (FGF); keratinocyte growth factor (KGF); transforming growth factors (TGF) β1 and β2; transforming growth factor (TGF) β3; platelet derived growth factor (PDGF); vascular endothelial growth factor (VEGF); tumor necrosis factor (TNF); interleukin-1 (IL-1) and interleukin-6 (IL-6); other interleukin/cytokine family members; insulin-like growth factor I (IGF-1); colony-stimulating factor 1 (CSF-1); and granulocyte macrophage colony stimulating factor (GM-CSF). Those skilled in the art will recognize that additional biologically active molecules can also be used in the methods and compositions of the invention.

In various embodiments, the extracellular matrix or matrix material used can be collagen, alginate, alginate beads, agarose, fibrin, fibrin glue, fibrinogen, blood plasma fibrin beads, whole plasma or components thereof, laminins, fibronectins, proteoglycans, HSP, chitosan, heparin, and/or other synthetic polymer or polymer scaffolds and solid support materials, such as wound dressings, that could hold or adhere to cells. In preferred embodiments, the extracellular matrix or matrix material is selected from the group consisting of fibrin, fibrin glue, fibrinogen, fibrin beads, and other synthetic polymer or polymer scaffolds or wound dressing materials.

In a further embodiment, the cell types are mitotically inactivated, e.g. induced to various stages of differentiation. For example, this mitotic inactivation can be accomplished by the administration of mitomycin C or other chemically-based mitotic inhibitors, irradiation with γ-Rays, irradiation with X-Rays, and/or irradiation with UV light.

In another embodiment, the cell types are immortalized using at least one gene/polypeptide selected from the group consisting of the 12S and 13S products of the adenovirus E1A genes, hTERT, SV40 small T antigen, SV40 large T antigen, papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus saimiri (HVS), mutant p53, myc, c-jun, c-ras, c-Ha-ras, h-ras, v-src, c-fgr, myb, c-myc, n-myc, and Mdm2.

In still further embodiments, the cell types are genetically engineered to secrete one or more biologically active molecules, such as at least one angiogenic factor, at least one growth/cytokine factor, or a combination of at least one angiogenic factor and at least one growth/cytokine factor. This secretion may be constitutive, or it may be controlled by gene switching.

In various other embodiments, the invention also provides methods of treating tissue defects or wounds by administering the cell preparations according to the invention to a wound site on a patient in need of wound treatment. The cell preparation of the invention can be administered locally (i.e. as a paste) to a wound site on a patient to temporarily induce tissue regeneration by biological interaction with surrounding tissues. Alternatively, the cell preparation of the invention can be administered by spraying the components on a wound site on a patient to temporarily induce tissue regeneration by biological interaction with surrounding tissues. The sprayed cell preparation may result in the formation of a matrix on the wound site.

In another aspect, the invention involves a method of manufacturing a cell preparation for tissue regeneration by providing a first composition containing one or more cells types that secrete one or more biologically active molecules admixed with thrombin, wherein the cells types are allogeneic, optionally mitotically inactivated, and selected from the group consisting of stromal, epithelial/organ specific, and blood derived cells. The first composition is then combined with a second composition containing an extracellular matrix or matrix material containing fibrinogen, wherein the combination of the first and second compositions forms a viscous cell past suitable for tissue regeneration. The cell types employed in the cell preparation may naturally secrete the one or more biologically active molecules, or they may be genetically engineered to secrete the one or more biologically active molecules.

In various embodiments, these cell types are differentiated fibroblasts and keratinocytes, and the biologically active molecule is at least one angiogenic factor, at least one growth/cytokine factor, or a combination of at least one angiogenic factor and at least one growth/cytokine factor. In other embodiments, the cell types may be mitotically inactivated by administration of mitomycin C or other chemically-based mitotic inhibitors, irradiation with γ-Rays, irradiation with X-Rays, or irradiation with UV light.

In other embodiments, the cell types are immortalized using at least one gene/polypeptide selected from the group consisting of the 12S and 13S products of the adenovirus E1A genes, hTERT, SV40 small T antigen, SV40 large T antigen, papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus saimiri (HVS), mutant p53, myc, c-jun, c-ras, c-Ha-ras, h-ras, v-src, c-fgr, myb, c-myc, n-myc, and Mdm2.

In another aspect, this invention provides a kit for the preparation of a cell preparation for tissue regeneration. This kit contains a first component containing an extracellular matrix or matrix material and a second component containing one or more cell types that secrete a biologically active molecule, such as, at least one angiogenic factor, at least one growth/cytokine factor, or a combination thereof. These cell types are allogeneic, mitotically active or inactivated, and selected from the group consisting of stromal, epithelial/organ specific and blood derived cells. For example, these cell types may be differentiated fibroblasts and keratinocytes. The resulting cell preparation can be in the form of a paste. In various embodiments, the extracellular matrix or matrix material can be fibrin, fibrin glue, fibrinogen, fibrin beads, and other synthetic polymer or polymer scaffolds or wound dressing materials.

Mitotic inactivation of the cells can be accomplished by administration of mitomycin C or other chemically-based mitotic inhibitors, irradiation with γ-Rays, irradiation with X-Rays, or irradiation with UV light. In various aspects, the cell types are immortalized using at least one of the following: the 12S and 13S products of the adenovirus E1A genes, hTERT, SV40 small T antigen, SV40 large T antigen, papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus saimiri (HVS), mutant p53, myc, c-jun, c-ras, c-Ha-ras, h-ras, v-src, c-fgr, myb, c-myc, n-myc, and Mdm2.

The cell types may naturally secrete the one or more biologically active molecules or they may be genetically engineered to secrete an exogenous level of the one or more biologically active molecules. Secretion may be controlled by gene switching or it may be constitutive. In one embodiment, the first component contains fibrinogen. In another embodiment, the first component contains fibrinogen and the second component contains from about $1 \times 10^3$ cells/µl to about $50 \times 10^3$ cells/µl. The second component also contains thrombin and can optionally contain a cryoprotectant such as a 10% glycerol solution, a 15% glycerol solution, and a 15% glycerol and 5% human serum albumin solution.

In another aspect, the invention provides methods for using the kits of the invention to prepare a cell preparation for tissue regeneration. This method involves administering the first component to a wound site on a patient in need of treatment and combining the second component with the first component on the would site, wherein the combination of the first and second components forms a cell preparation suitable for tissue regeneration. In one embodiment, the first and second components are topically administered to the wound site on the patient. In another embodiment, the first and second components are sprayed onto the wound site. The components can be sprayed such that they are combined on the wound or such that they are combined in the air before reaching the wound.

In yet another aspect, the invention provides methods of administering a cell preparation for tissue regeneration to a wound site on a patient in need of treatment. This method involves the steps of providing a first component containing an extracellular matrix or matrix material containing fibrinogen; providing a second component containing from about $1 \times 10^3$ cells/µl to about $50 \times 10^3$ cells/µl and thrombin, wherein the cells secrete one or more biologically active molecules, are allogeneic, mitotically active or inactivated, and selected from the group consisting of stromal, epithelia/organ specific, and blood-derived cells; combining the first and second components to form a cell preparation suitable for tissue regeneration; and administering the cell preparation to the wound site.

In one embodiment, the first and second components are topically applied to the wound site. The first component can be applied to the wound site before or after the second component is applied. In another embodiment, the first and second components are sprayed on the wound site. Preferably, the first component is sprayed on the wound site before the second component is sprayed on the wound site. The first and second components may be combined on the wound site or they may be combined before reaching the wound site.

These cell types may be differentiated or undifferentiated fibroblasts and keratinocytes. The resulting cell preparation can be in the form of a paste. In various embodiments, the extracellular matrix or matrix material can be fibrin, fibrin glue, fibrinogen, fibrin beads, and other synthetic polymer or polymer scaffolds or wound dressing materials. Mitofic inactivation of the cells can be accomplished by administration of mitomycin C or other chemically-based mitotic inhibitors, irradiation with γ-Rays, irradiation with X-Rays, or irradiation with UV light. In various embodiments, the cell types are immortalized using at least one of the following: the 12S and 13S products of the adenovirus E1A genes, hTERT, SV40 small T antigen, SV40 large T antigen, papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus saimiri (HVS), mutant p53, myc, c-jun, c-ras, c-Ha-ras, h-ras, v-src, c-fgr, myb, c-myc, n-myc, and Mdm2.

The cell types may naturally secrete the one or more biologically active molecules or they may be genetically engineered to secrete an exogenous level of the one or more biologically active molecules. Secretion may be controlled by gene switching or it may be constitutive. In one embodiment, the second component can optionally contain a cryoprotectant including, but not limited to, a 10% glycerol solution, a 15% glycerol solution, and a 15% glycerol and 5% human serum albumin solution.

In another aspect, the invention involves a cell preparation for tissue regeneration containing an extracellular matrix or matrix material containing fibrinogen admixed with a second component containing from about $1 \times 10^3$ cells/µl to about $50 \times 10^3$ cells/µl and thrombin, wherein the cells secrete one or more biologically active molecules (such as at least one angiogenic factor, at least one growth/cytokine factor, or combinations thereof) are allogeneic, mitotically inactivated, and selected from the group consisting of stromal, epithelia/organ specific, and blood-derived cells.

These cell types may be differentiated fibroblasts and keratinocytes. The resulting cell preparation can be in the form of a paste. In various embodiments, the extracellular matrix or matrix material can be fibrin, fibrin glue, fibrinogen, fibrin beads, and other synthetic polymer or polymer scaffolds or wound dressing materials. Mitotic inactivation of the cells can be accomplished by administration of mitomycin C or other chemically-based mitotic inhibitors, irradiation with γ-Rays, irradiation with X-Rays, or irradiation with UV light. In various embodiments, the cell types are immortalized using at least one of the following: the 12S and 13S products of the adenovirus E1A genes, hTERT, SV40 small T antigen, SV40 large T antigen, papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus saimiri (HVS), mutant p53, myc, c-jun, c-ras, c-Ha-ras, h-ras, v-src, c-fgr, myb, c-myc, n-myc, and Mdm2.

The cell types may naturally secrete the one or more biologically active molecules or they may be genetically engineered to secrete an exogenous level of the one or more biologically active molecules. Secretion may be controlled by gene switching or it may be constitutive. In one embodiment, the second component can optionally contain a cryoprotectant including, but not limited to a 10% glycerol solution, a 15% glycerol solution, and a 15% glycerol and 5% human serum albumin solution.

The invention also provides methods of using such cell preparations by providing the first and second components, combining the first and second components and administering the resulting cell preparation to the wound site. In various embodiments, the components can be topically administered to the wound site on the patient or they can be sprayed onto the wound site. When spray administered, the first and second components can be combined on the wound site or they can be combined before reaching the wound site.

In another aspect, the first and second components of the kits of the invention is cryopreserved prior to shipping and subsequently thawed prior to use. Each component may be contained in a separate vial having a removable screw cap, wherein the vial is sterile and is made of a material resistant to low temperatures and wherein the removable lid can be replaced with a spray pump following thawing of the first and second components prior to use. In one embodiment, the spray pump delivers a volume of approximately 130 μl per spray. Suitable materials resistant to low temperatures include, but are not limited to, glass, polypropylene, polyethylene, and ethylene vinyl acetate (EVA). In some embodiments, each vial may have a wall thickness of approximately 0.8 ml and may hold a working volume of approximately 2 ml of the first and second components. In another embodiment, the vials are sealed within a pouch or container prior to cryopreservation, wherein the pouch or container is fabricated of a material capable of withstanding temperatures ranging from −80° C. to −160° C. and wherein the pouch or container protects the first and second components from contamination during cryopreservation, storage, and subsequent thawing. Preferable, the pouch is waterproof and has a high barrier performance.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 3 is a table showing the results of testing for optimal dilutions of thrombin and fibrinogen for the formulation of a spray applied fibrin glue matrix.

FIG. 6a is a cross section of the vial. FIG. 6b is a three-dimensional drawing of the outside of the vial, which is designed to hold a working volume of 2 ml of the component.

FIG. 11 is a histogram showing growth factor secretion by frozen cell preparations stored frozen for one week at −80° C. Results for various keratinocyte:fibroblast ratios and number of cells are shown.

DETAILED DESCRIPTION OF THE INVENTION

Figure 1:
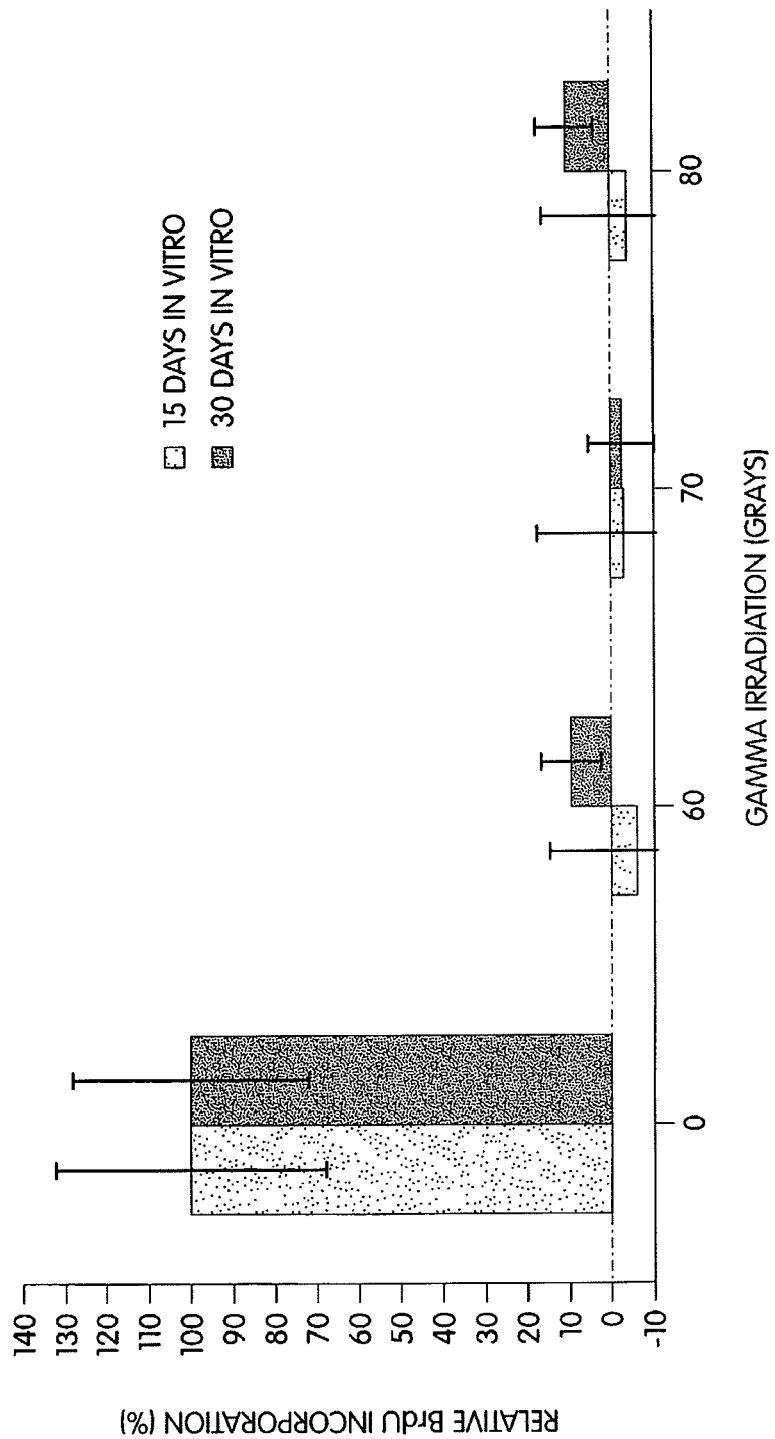
FIG. 1 is a histogram showing the results of a BrdU cell proliferation analysis of human primary fibroblasts following 15 and 30 days in culture after gamma irradiation.

Wound healing is a complex process involving soluble mediators, blood cells, extracellular matrix, and parenchymal cells. Wound healing has three phases—the inflammation phase, the tissue formation phase, and the tissue remodeling phase. These phases may overlap in time.

Generally, an injury to tissue disrupts blood vessels and leads to extravasation of blood constituents. Blood clotting helps to reestablish hemostasis and provides a provisional extracellular matrix for cell migration to the wound. At the wound site, platelets (thrombocytes) facilitate the formation of a hemostatic plug and also secrete several mediators of the wound healing process. These mediators include, for example, molecules such as platelet-derived growth factor that attract and activate monocytes and fibroblasts.

Soon after the injury, neutrophils infiltrate the wound and clean the wound of foreign particles and bacteria. The neutrophils are then extruded with the eschar or undergo phagocytosis by macrophages. Monocytes also infiltrate the wound in response to specific chemoattractants, such as fragments of extracellular matrix proteins, transforming growth factors β, the monocyte chemoattractant protein 1, and subsequently become activated macrophages. These activated macrophages release growth factors such as platelet-derived growth factor and vascular endothelial growth factor, which initiate the formation of granulation tissue. Macrophages bind through their integrin receptors to proteins in the extracellular matrix. This binding stimulates macrophage phagocytosis of any microorganisms as well as of fragments of extracellular matrix.

Monocytes, stimulated by adherence to the extracellular matrix, also undergo metamorphosis into inflammatory macrophages. This adherence to the extracellular matrix induces monocytes and macrophages to express colony-stimulating factor 1, tumor necrosis factor β, and platelet derived growth factor. Other important cytokines expressed by monocytes and macrophages are transforming growth factor α, interleukin-1, transforming growth factors β 1-3, and insulin-like growth factor 1. The monocyte- and macrophage-derived growth factors are thought necessary for the initiation and propagation of new tissue formation in wounds.

Within hours after the injury, reepithelialization of wounds begins. Keratinocytes from the wound edges as well as from residual skin appendages such as hair follicles undergo marked changes in phenotype, including retraction of intracellular tonofilaments, dissolution of most intercellular desmosomes, and formation of peripheral cytoplasmic actin filaments. Furthermore, the hemidesmosomal links between the keratinocytes and the epidermal basement membrane dissolves, allowing the movement of keratinocytes.

Within a few days post injury, the keratinocytes at the margin of the wound begin to proliferate behind the migrating cells. As this reepithelialization occurs, the basement-membrane proteins reappear in an ordered sequence from the margin of the wound outward. Keratinocytes then revert to their normal phenotype and attach themselves to the reestablished basement membrane and underlying dermis.

Within about four days post injury, new stroma begins to infiltrate the wound. Concomitantly, macrophages, fibroblasts, and blood vessels also infiltrate the wound. Macrophages provide a source of growth factors that stimulate fibroplasia and angiogenesis. The fibroblasts produce the new extracellular matrix that supports cell in-growth. The new blood vessels carry oxygen and nutrients that sustain the cells.

Growth factors, particularly platelet-derived growth factor and transforming growth factor β1, are thought to stimulate fibroblasts of the tissue around the wound to proliferate. In fact, platelet-derived growth factor has been shown to accelerate the healing of chronic pressure sores and diabetic ulcers. Basic fibroblast growth factor has also been used with some success to treat chronic pressure sores.

However, there are many factors that can lead to abnormal wound healing. One example occurs with diabetic ulcers. Typically, diabetic ulcers exhibit multiple biochemical pathologies that can lead to impaired healing. These ulcers occur in patients who cannot sense and relieve cutaneous pressure due to some type of diabetic neuropathy. Frequently, diabetic ulcers become infected because of impaired granulocytic function and chemotaxis. Patients with diabetic ulcers also experience inflammation, impaired neovascularization, decreased synthesis of collagen, increased levels of proteinases, and defective macrophage function.

Overall clinical experience using isolated, e.g., recombinant, growth factors and other mediators to accelerate wound healing has not met with great success, perhaps because wound repair is the result of a complex set of interactions between soluble factors, formed blood elements, extracellular matrix, and cells. Combining various growth factors at carefully controlled intervals may promote more effective wound healing.

The present invention provides stromal, epithelial, and blood-derived cells, including, but not limited to, fibroblasts, keratinocytes including follicular outer root sheath cells, endothelial cells, pericytes, monocytes, lymphocytes including plasma cells, thrombocytes, mast cells, adipocytes, muscle cells, hepatocytes, nerve and neuroglia cells, osteocytes, osteoblasts, corneal epithelial cells, and chondrocytes that are admixed with either a synthetic or natural extracellular matrix ("ECM") to form a cell preparation that can be used to improve tissue granulation during wound healing. In one embodiment, the cells may deliver endogenous angiogenic factors or other growth factors. In another embodiment, the cells can be genetically engineered to produce exogenous amounts of the desired factor. Preferably, the cells are allogeneic. Those skilled in the art will recognize that the cells employed in the methods and preparations of the invention may include, but are not limited to, living cells, mitotically inactivated cells, mitotically activated cells, metabolically inactive cells, lyophilized cells and/or nonliving cells.

In particular, fibroblasts and keratinocytes have been shown to play an important role in cutaneous wound healing. These roles include stimulating cell migration and proliferation, stimulating extracellular matrix production, producing growth factors and cytokines, stimulating angiogenesis, and releasing proteases which dissolve non-viable tissue and the fibrin barrier.

Wound healing may be promoted by use of growth and/or angiogenic factors. For example, one suitable wound healing preparation consists of two cryopreserved components, i.e., fibrinogen and growth-arrested, allogeneic human fibroblasts and keratinocytes suspended in thrombin. After thawing, these components are sprayed sequentially on the wound bed to form a thin fibrin matrix containing two types of living, but not proliferating skin-derived cells, which, for several days, interactively produce growth and angiogenic factors relevant for wound healing (e.g. VEGF, GM-CSF, bFGF, KGF).

The cells may be either immortalized or primary cell cultures. Cells may be immortalized by any method known to those skilled in the art. A common approach to lengthening the lifespan of a cell is to transfer a virus or a plasmid that contains one or more immortalizing genes. Cell immortalization increases the lifespan of a cell, and the resulting cell line is capable of being passaged many more times than the original cells. Immortalizing genes are well known in the art. See, e.g., Katakura et al., *Methods Cell Biol.* 57: 69-91 (1998). Immortalizing proteins or polypeptides include, but are not limited to, the 12S and 13S products of the adenovirus E1A genes, SV40 small and large T antigens, papilloma viruses E6 and E7, the Epstein-Barr Virus (EBV), Epstein-Barr nuclear antigen-2 (EBNA2), human T-cell leukemia virus-1 (HTLV-1), HTLV-1 tax, Herpesvirus Saimiri (HVS), mutant p53, and the proteins from oncogenes such as myc, c-jun, c-ras, c-Haras, h-ras, v-src, c-fgr, myb, c-myc, n-myc, and Mdm2. Additionally, cells may become spontaneously immortalized. A preferred immortalization strategy is by transfer of the gene encoding telomerase reverse transcriptase (TERT) into the cell such that TERT was either stably or transiently expressed thereby resulting in the expression of telomerase activity. Telomerase activity, when expressed in normal somatic cells, can lead to elongation of the chromosome tips or protective caps, called telomeres, thereby resulting in the ability of the telomerase expressing cells to become immortalized without becoming transformed (See Jiang, et al., Nature Genetics 21:111-14 (1999) and Morales, et al., Nature Genetics 21:115-18 (1999)).

Telomeres are specialized structures at the ends of eukaryotic chromosomes and that appear to function in chromosome stabilization, positioning, and replication. See Blackburn & Szostak, 53 Ann. Rev. Biochem. 163-194 (1984); Zakian, 23 Ann. Rev. Genetics 579-604 (1989); Blackburn, 350 Nature 569-573 (1991). In all vertebrates, telomeres consist of hundreds to thousands of tandem repeats of the 5'-TTAGGG-3' sequence and associated proteins. See Blackburn, 350 Nature 569-573 (1991); Moyzis et al., 85 Proc. Natl. Acad. Sci. 6622-6626 (1988). Southern blot analysis of chromosome terminal restriction fragments (TRF) provides the composite lengths of all telomeres in a cell population. See Harley et al., 3445 Nature 458-460 (1990); Allsopp et al., 89 Proc. Natl. Acad. Sci. USA 10114-10118 (1992); Vaziri et al., 52 µm. J. Human Genetics 661-667 (1993). In all normal somatic cells examined to date, TRF analysis has shown that the chromosomes lose about 50-200 nucleotides of telomeric sequence per cell division, consistent with the inability of DNA polymerase to replicate linear DNA to the ends. See Watson, 239 Nature New Biology 197-201 (1972).

This shortening of telomeres has been proposed to be the mitotic clock by which cells count their divisions (see Harley, 256 Mut. Res. 271-282 (1991)), and sufficiently short telomeres may be the signal for replicative senescence in normal cells. See Hastie et al., 346 Nature 866-868 (1990); Lindsey et al., 256 Mut. Res. 45-48 (1991); Wright & Shay, 8 Trends Genetics 193-197 (1992). In contrast, the vast majority of immortal cells examined to date show no net loss of telomere length or sequence with cell divisions, suggesting that maintenance of telomeres is required for cells to escape from replicative senescence and proliferate indefinitely. See Counter et al., 11 EMBO 1921-1929 (1992); Counter et al., 91 Proc. Natl. Acad. Sci. USA 2900-2940, 1994).

Telomerase, a unique ribonucleoprotein DNA polymerase, is the only enzyme known to synthesize telomeric DNA at chromosomal ends using as a template a sequence contained within the RNA component of the enzyme. See Greider & Blackburn, 43 Cell 405-413 (1985); Greider & Blackburn, 337 Nature 331-337 (1989); Yu et al., 344 Nature 126-132 (1990); Blackburn, 61 Ann. Rev. Biochem. 113-129 (1992). With regard to human cells and tissues, telomerase activity has been identified in immortal cell lines and in ovarian carcinoma but has not been detected in mortal cell strains or in normal non-germline tissues. See Morin, 59 Cell 521-529, 1989. Together with TRF analysis, these results suggest telomerase activity is directly involved in telomere maintenance, linking this enzyme to cell immortality.

Expression of the human telomerase catalytic component (hTERT) has recently been studied in human somatic cells. See Jiang, et al., 21 Nature Genetics 111-114 (1999). Telomerase expression in normal somatic cells did not appear to induce changes associated with a malignant phenotype such as abnormal growth control or oncogenic transformation. The absence of cancer-associated changes was also reported in human fibroblasts immortalized with telomerase. See Morales, et al., 21 Nature Genetics 115-118 (1999). It was demonstrated that the introduction of telomerase into normal human somatic cells does not lead to growth transformation, does not bypass cell-cycle induced checkpoint controls and does not lead to genomic instability of these cells. Methods for detecting telomerase activity, as well as for identifying compounds or polypeptides that regulate or affect telomerase activity, together with methods for therapy or diagnosis of cellular senescence and immortalization by controlling or measuring telomere length and telomerase activity, have also been described (see PCT International patent application WO 93/23572). The identification of compounds affecting telomerase activity provides important benefits to efforts at treating human disease.

The cells according to the invention can also be genetically engineered to produce one or more of biologically active molecules such that the molecules are constitutively secreted from the cells. By "constitutively secreted" is meant that the desired biologically active molecule is continuously expressed by the cells or that the gene is continually expressed. Alternatively, the cells can be genetically engineered such that their expression is controlled by gene switching.

As used herein, the terms "gene switch" and "gene switching" refer to methods of regulating gene expression. Specifically, expression of a protein encoded by a gene is controlled by the interaction of certain regulatory proteins, known as DNA-binding proteins, with a region located upstream of the gene. Within the promoter region, there are located several operator regions which contains a specific oligonucleotide sequence to which these DNA-binding proteins specifically bind. These proteins can lead either to activation or repression of gene expression. Thus, they control the regulated expression of genes.

The regulator protein is encoded by a regulatory gene located elsewhere on the chromosome. The interaction of regulator and operator is affected by the presence or absence of particular chemical factors (inducers). Thus, in normal circumstances the regulator is expressed, thereby binding the operator and inhibiting expression of the gene, until a need for the particular protein encoded by the gene is indicated by the appearance in the environment of a specific inducer which interacts with the regulator to inhibit binding to the operator, thus allowing expression of the gene.

For example, an enzyme, which acts upon a sugar molecule is not required unless that sugar is present and, therefore, in the absence of the sugar, the regulatory gene expresses the regulator protein, which binds the gene operator and inhibits expression of the enzyme. The sugar itself acts as the inducer, which then interacts with the regulator to prevent its binding to the operator thus allowing expression of the enzyme. Digestion of the sugar by the enzyme removes it from the environment allowing the regulator to return to its normal mode and act normally to inactivate enzyme expression.

Such a regulatory mechanism can be viewed as a switching arrangement which switches gene expression on and off as dictated by the chemical content of the environment. Gene switching systems of the type described are best known in bacteria and many of the proteins and their target DNA binding sites are known in considerable detail. The regulator proteins usually bind as dimers to operators, which exhibit a two-fold symmetry. The specificity of the regulator/promoter interaction is determined by the sequence specific interaction of specific amino acids of the regulator with the operator DNA. In some systems interactions have been subject to detailed biochemical analysis as well as high resolution X-ray crystallography. The best-characterized class of DNA binding proteins exhibit a common helix-turn-helix motif with some degree of amino acid sequence homology. It is clear that the critical DNA binding domain of the regulator is contained within the helix-turn-helix region.

In eukaryotes it has been shown that control of gene expression is also regulated by the interaction of specific protein factors binding to DNA sequences close to the promoter region of genes. A number of factors have been isolated from yeast and mammalian cells and have been shown to interact with specific sequence motifs in a sequence-specific manner similar to that observed in bacterial systems. Characterization of some of these factors has revealed a new "finger" motif, which may be involved in the sequence specific binding of proteins.

Moreover, it has been demonstrated that eukaryotic gene expression can be controlled through the use of bacterial repressor molecules in eukaryotic cells. In these experiments bacterial operator sequences have been inserted close to the promoters of mammalian genes. Cell lines have been created which express the bacterial repressor. Control of expression of the target eukaryotic genes with operator insertions by repressor molecules has been demonstrated using transient expression assays. In these experiments not only repression of gene expression by the lac repressor has been demonstrated but also induction of gene expression, that is, relief of repression, using IPTG (isopropyl thiogalactoside).

Therefore, detailed knowledge and manipulation of bacterial protein DNA/interactions can be used to control expression in mammalian cell cultures. Gene switching techniques are described, for example in U.S. Pat. No. 6,010,887, which is incorporated herein by reference. Those of ordinary skill in this art will recognize that other methods of gene switch regulation may also be employed in the methods and compositions of the invention.

Although non-genetically modified cells may be used in accordance with the invention, in one preferred embodiment, the isolated cells are genetically engineered. The cells can be genetically engineered to secrete one or more biologically active molecules including, but not limited to, one or more cytokines, growth factors, and/or angiogenic factors, or a combination thereof. Examples of such biologically active molecules are provided in Table 1.

TABLE 1

| Cytokine | Major Source | Target Cells and/or Major Effects |
|---|---|---|
| Epidermal growth factor (EGF) | Platelets | Pleiotropic-cell motility and proliferation |
| Transforming growth factor "alpha" (TGFα) | Macrophages, epidermal cells | Pleiotropic-cell motility and proliferation |
| Heparin-binding epidermal growth factor | Macrophages | Pleiotropic-cell motility and proliferation |
| Basic fibroblast growth factor | Macrophages, endothelial cells | Angiogenesis and fibroblast proliferation |
| Acidic fibroblast growth factor | Macrophages, endothelial cells | Angiogenesis and fibroblast proliferation |
| Keritinocyte growth factor | Fibroblast | Epidermal-cell motility and proliferation |
| Transforming growth factor β family (TGFβ) | | Fibrosis and increased tensile strength |
| Transforming growth factors β1 and β2 (TGFβ1 & TGFβ2) | Platelets, macrophages | Epidermal-cell motility, chemotaxis of macrophages and fibroblasts, extracellular matrix synthesis and remodeling |
| Transforming growth factor β3 (TGFβ3) | Macrophages | Antiscarring effects |
| Platelet derived growth factor (PDGF) | Platelets, macrophages, epidermal cells | Fibroblast proliferation and chemoattraction, macrophage chemoattraction and activation |
| Vascular endothelial growth factor (VEGF) | Epidermal cells, macrophages; endothelial cells | Angiogenesis and increased vascular permeability |
| VEGF A | Blood vessel endothelial cells | Endothelial cell migration and blood vessel formation |
| VEGF B | Blood vessel endothelial cells | Endothelial cell migration and blood vessel formation |
| VEGF C | Lymphatic vessel endothelial cells | Endothelial cell migration and lymphatic vessel formation |
| VEGF D | Lymphatic vessel endothelial cells | Endothelial cell migration and lymphatic vessel formation |
| Tumor necrosis factor "alpha" (TNFα) | Neutrophils | Pleiotropic expression of growth factors |
| Interleukin-1 (IL-1) | Neutrophils | Pleiotropic expression of growth factors |
| Insulin-like growth factor I | Fibroblasts, epidermal cells | Reepithelialization and granulation-tissue formation. |
| Colony-stimulating factor 1 (CSF-1) | Multiple cells | Macrophage activation and granulation tissue formation. |
| Granulocyte | Multiple cells | Macrophage activation and |

TABLE 1-continued

| Cytokine | Major Source | Target Cells and/or Major Effects |
|---|---|---|
| Macrophage colony stimulating factor (GM-CSF) | | granulation tissue formation |

Column 1 of Table 1 names suitable biologically active molecules. Column 2 displays the major source of the particular biologically active molecule. Finally, Column 3 shows the target cells and/or major effect of the given biologically active molecule.

Fibroblasts and keratinocytes naturally secrete a vast array of growth factors and cytokines. A summary of the secretion of various proteins is shown in Table 2:

TABLE 2

| Cytokines | Keratinocytes | Fibroblasts |
|---|---|---|
| Angiopoietin | Yes | yes |
| EGF | Yes | yes |
| Endothelin | Yes | no |
| FGFs | Yes | yes |
| FGF-7/KGF | Yes | yes |
| IFN-α/β | no | yes |
| IGF-1 | no | yes |
| IL-1β | yes | yes |
| IL-6 | yes | yes |
| IL-8 | yes | yes |
| IL-18 | yes | no |
| MCP-1 | no | yes |
| MIP-1α | no | yes |
| MIP-2 | no | yes |
| PDGF | no | yes |
| SLPI | yes | no |
| TGF-α | yes | yes |
| TGF-βs | yes | yes |
| TNF-α | yes | yes |
| VEGF | yes | yes |

(See Singer, A. and Clark, R. (1999) "Cutaneous Wound Healing" The New England Journal of Medicine 341:738: 746.)

Control of the delivery of the secreted biologically active molecule can be achieved by any method known to those skilled in the art. For example, the expression of multiple gene products may be controlled by a single promoter system. Alternatively, the expression of multiple gene products may be controlled by multiple promoter systems, with each promoter system regulated either constitutively, by gene switching or by some combination of both. Further, control over the secretion of a particular biologically active molecule may be accomplished by up-regulating wild-type gene expression.

A number of well-known transfection methods exist for introducing genetic material into target cells. These include the use of polycations such as DEAE-dextran (see McCutchan, et al., J. Natl. Cancer Inst. 41:351-57 (1968) and Kawai et al., Mol. Cell. Biol. 4:1172-74 (1984)); calcium phosphate coprecipitation (see Graham et al., Virology 52:456-67 (1973)); electroporation (see Neumann et al, EMBO J. 7:841-45 (1982)); lipofection (see Felgner et al., Proc. Natl. Acad. Sci. USA 84:7413-17 (1987)); retrovirus vectors (see Cepko et al., Cell 37:1053-62 (1984)); and microinjection (see Capecchi et al., Cell 22:479-88 (1980)).

Moreover, one skilled in the art will recognize that any other method suitable for delivering an exogenous biologically active molecule into the cell types may also be employed in accordance with the invention.

Using any of the above-mentioned transfection methods, control over the secretion of a variety of biologically active molecules may be achieved by employing any number of cell types secreting the various biologically active molecules.

Additionally, the cell types of the present invention may also be either mitotically active or mitotically inactive. The term "mitotically active" is used to describe cells that actively undergo mitosis. Conversely, "mitotically inactive" is used to describe cells that do not actively undergo mitosis. Mitotically inactive cells may be growth arrested by any means known in the art. By way of non-limiting example, the cells may be growth arrested by chemical means, such as, for example, by the administration of mitomycin C. Additionally, the cell types may be growth arrested by exposure to UV light, X-Ray, or gamma (γ) radiation. In one preferred embodiment, the cell types are growth arrested by exposure to gamma radiation. It is important to note that, e.g., mitotically inactivated, human fibroblast cells terminally differentiate and thereby change the pattern of polypeptide expression and secretion (Francz, Eur. J. Cell. Biol. 60:337-45 (1993)). As a further example, keratinocyte differentiation usually depends on culture conditions (including, for example, the composition of culture media, the $Ca^{2+}$-concentration, and whether the cells are cultured at the air-liquid interface), however, keratinocytes may also be induced to differentiate, e.g., by mitomycin C.

The cell types according to the invention may be autologous, allogeneic, or xenogeneic. Most preferably, the cell types used in the present invention are allogeneic. Xenogeneic cells can be isolated for example from transgenic animals expressing molecules of interest.

Stromal cells including, for example, fibroblasts, can be isolated by any method known to those skilled in the art. For example, fibroblasts may be derived from organs, such as skin, liver, and pancreas. These organs can be obtained by biopsy (where appropriate) or upon autopsy. Specifically, sufficient quantities of fibroblasts can be obtained rather conveniently from breast reduction, foreskin, or any appropriate cadaver organ.

Fibroblasts can be readily isolated by disaggregating an appropriate source organ or tissue. By "source organ or tissue" is meant the organ or tissue from which the cells are obtained. Disaggregation may be readily accomplished using techniques known to those skilled in the art. Examples of such techniques include, but are not limited to mechanical disaggregation and/or treatment with digestive enzymes and/or chelating agents that weaken the connections between neighboring cells thereby making it possible to disperse the tissue into a suspension of individual cells without appreciable cell breakage. Specifically, enzymatic dissociation can be accomplished by mincing the tissue and treating the minced tissue with any of a number of digestive enzymes, either alone or in combination. Suitable enzymes include, but are not limited to, trypsin, chymotrypsin, collagenase, elastase, hyaluronidase, DNase, pronase, and/or dispase. Mechanical disruption can be accomplished by a number of methods including, but not limited to, the use of grinders, blenders, sieves, homogenizers, pressure cells, insonators or trituration. See Freshney, Culture of Animal Cells. A Manual of Basic Technique, 2d Ed., A.R. Liss, Inc., New York, 1987, Ch. 9, pp. 107-26.

Once the source tissue has been reduced to a suspension of individual cells, the suspension should be fractionated into subpopulations from which the fibroblasts and/or other stromal cells and/or elements can be recovered. Fractionation may be accomplished using standard techniques for cells separation including, but not limited to, cloning and selection of specific cells types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. See Freshney, Culture of Animal Cells. A Manual of Basic Techniques, 2d Ed., A.R. Liss, Inc., New York, 1987, Ch. 11 and 12, pp. 137-68. Those skilled in the art will recognize that other suitable cell fractionation technique(s) can also be used.

Preferably, the isolation of fibroblasts is accomplished by explantation of skin pieces according to the method of Sly and Grubb. See Sly et al., Methods Enzymol. 58:444-50 (1979).

Fibroblasts obtained from different source organs or tissues (including, e.g., skin, liver, and pancreas) can be employed in the methods and compositions of the invention. Moreover, those skilled in the art will recognize that any such fibroblasts can be genetically engineered to secrete differing amounts of a biologically active molecule or molecules.

As used herein, the term "cell preparation" refers to the mixture resulting from the combination of a preparation of cells that secrete one or more biologically active molecules and a preparation of the extracellular or other matrix materials. For example, a cell preparation according to the invention results from the combination of a thrombin/cell preparation and a fibrinogen preparation. In some embodiments, the resulting mixture results in polymerization, thereby producing a cured matrix. Alternatively, the resulting combination may produce a highly viscous, non-cured matrix. The resulting cell preparation can be in the form of a paste. Those skilled in the art will recognize that as used herein, the term "cell preparation" encompasses a spectrum of mixtures ranging from a viscous, non-cured mixture (i.e. a paste) to a polymerized, cured matrix. Differences in the concentration of each preparation as well as the culture conditions can influence the viscosity and/or the degree of polymerization of the resulting cell preparation. For example, in one embodiment of the invention, the combination of the fibrinogen and the thrombin/cell preparations are spray administered to a wound site to form an irreversible, polymerized cell matrix. However, those skilled in the art will also recognize that other combinations may result in a viscous, non-cured cell matrix.

To create the cell preparation according to the invention, the cell types or genetically engineered cell lines are preferably admixed or combined with a supporting biological or synthetic extracellular matrix or matrix material (ECM). One skilled in the art will recognize that the term "ECM" refers to the noncellular material distributed throughout the body of multicellular organisms. The ECM is comprised of diverse constituents such as glycoproteins, proteoglycans, complex carbohydrates, and other molecules. Major functions of the ECM include, but are not limited to, providing structural support, tensile strength or cushioning; providing substrates and pathways for cell adhesion and cell migration; and regulating cellular differentiation and metabolic function. ECM proteins include, for example, collagens, elastin, fibronectin, laminin, proteoglycans, vitronectin, thrombospondin, tenascin (cytoactin), entactin (nidogen), osteonectin (SPARC), anchorin CII, chondronectin, link protein, osteocalcin, bone sialoprotein, osteopontin, epinectin, hyaluronectin, amyloid P component, fibrillin, merosin, s-laminin, undulin, epilligrin, and kalinin. Preferred ECM proteins for use according to this invention include collagen, alginate, agarose, fibrin, fibrin glue, fibrinogen, laminins, fibronectins, HSP, chitosan, heparin and/or other synthetic polymer or polymer scaffolds.

Cell density and the concentration of the extracellular matrix may be varied for the desired clinical application. For example, certain wounds may require greater or lesser cell densities and/or different consistency preparations. The resulting cell preparations can be in the form of a cell paste or in the form of a cured matrix. Determination of the appropriate cell density and concentration of the ECM is within the routine skill of those in the art. The cell suspension can come from one cell type or can be comprised of a mixture of different cell types. For example, the cell mixture may include 50% of keratinocytes and 50% of fibroblasts. However, the ratio of keratinocytes to fibroblasts may be varied, e.g. 1:1, 1:4, 1:9, 1:24 etc. without impairing the formation or the function of the cell preparation. Alternatively, the cell mixture may contain only keratinocytes or only fibroblasts (i.e., the ratio of keratinocytes to fibroblast may be 1:0 or 0:1). Moreover, the suspension may be comprised of more than two different cell types. The percentages of each cell type in the cell suspension may vary depending on the intended use for the cell preparation. The cell types can also be pre-induced or co-cultured in vitro in order to optimize the healing response on the wound. For example, fibroblasts can be pre-incubated with TGF-beta (from 0.1 to 30 ng/ml of medium) for 1 to 21 days prior to wound application.

The cell preparation of the invention is made from two components. The first, referred to herein as "component #1" is the fibrinogen component. The second, referred to herein as "component #2" is the cells+thrombin component. Component #2 can optionally contain a cryoprotectant. The cell preparation of the invention is formed by the coagulation of plasma proteins (including fibrinogen) in the presence of thrombin. This coagulation is chiefly due to the formation of a polymerized fibrin network, which imitates the formation of a blood clot. Thrombin converts fibrinogen to fibrin by enzymatic cleavage. Calcium accelerates the proteolytic activity of thrombin. In fact, the combination of fibrinogen and thrombin results in a "polymerization reaction". Upon mixing of these materials, the cells become entrapped in the resulting cell preparation, which may be a paste or a cured matrix, depending on the concentrations of all components, the number of cells, the culture conditions, etc. Additionally, in any of the cell preparations of the invention, any or all of the components may also contain additional proteins or chemicals, which do not affect the formation or function of the cell preparation, such as proteins (i.e. Albumin), proteinase inhibitors (i.e., Aprotinin), polyethylene glycol (PEG), polyvinyl alcohol (PVA), and other molecules typically used as stabilizers for cell preparations. In other embodiments of the invention, the first component of the cell preparation may contain thrombin and the second component may contain cells plus fibrinogen. Those skilled in the art will recognize that, in this embodiment, the combination of component #1 and component #2 will also result in a cell preparation useful for tissue regeneration. Moreover, in other embodiments, the cell preparations suitable for tissue regeneration may result from "synthetic polymerization" rather than from polymerization following the interaction of fibrinogen and thrombin.

In this embodiment, the cells are mixed with a polymerization agent, either before or after application to the wound site. Once polymerization occurs, a cell preparation suitable for tissue regeneration may be formed.

While the compositions, cell preparations, kits, and/or methods described herein refer to the use of a first component containing fibrinogen and a second component containing cells+thrombin, other components may also be used. Examples of such components include the thrombin component #1 and the cells+fibrinogen component #2 as well as the components leading to synthetic polymerization, which are discussed in detail above. Those skilled in the art will recognize that any of the compositions, cell preparations, kits, and/or methods described herein using the fibrinogen component #1 and the cells+thrombin component #2 may also employ any other combination of components which result in a cell preparation for tissue regeneration in which the cells become entrapped in the resulting paste or matrix, without deviating from the nature of the invention.

Methods of Administration

In one preferred embodiment, the invention involves a combination of human allogeneic fibroblast and keratinocyte cell lines admixed with ECM materials to form a viscous cell paste to adhere to a wound. In this embodiment, the cell lines are preferably not genetically engineered. The cell lines may be mitotically inactivated by any means known to those skilled in the art. Preferably, the resulting paste is both biodegradable and biocompatible. The paste may be applied to the wound as needed, for example, once weekly. Application of the cell paste according to this embodiment facilitates the induction of granulation tissue and the stimulation of wound closure.

As previously described, immortalized fibroblast and keratinocyte cell lines would also be preferred embodiments. The preferred immortalization method would be through directly adding the gene for TERT into the primary human keratinocyte and fibroblast cells such that the TERT gene is constitutively expressed. In addition, a transient immortalization using a protein domain transport sequence (TAT, VP22, MTS, etc. attached to the TERT protein might be more preferable in that the gene is not permanently inserted into the immortalized cell but is instead added as a fusion protein to the growth medium. In this way, the cell line could be continuously expanded, banked, and screened for stable properties (growth rate, factor secretion, etc.), without the continual need for the revalidation of new primary cell sources. Cell lines immortalized in this way would preferentially be mitotically inactivated before application to the wound or tissue repair site as a paste, cell preparation, biological matrix mixture, or as attached or adsorbed to a wound dressing.

The present invention has human clinical and veterinary applications. The cell preparation of the invention can be used to treat humans and non-human animals, including, a non-human primate, mouse, rat, dog, cat, pig, sheep, cow, or horse. The cell preparation according to the invention can be used for tissue regeneration such as, e.g., in skin wound treatment or in treatment of peritonitis.

For example, the cell preparation of the invention can be incorporated into other pharmaceutical compositions suitable for administration. Such compositions can comprise the cell preparation and an additional acceptable carrier. As used herein, "biologically acceptable carrier" is intended to include any and all solvents, dispersion media, coatings, antibacterial, and antifungal agents, isotonic and absorption delaying agents, and the like, compatible with biologics administration. Suitable carriers are described in the most recent edition of Remington's Pharmaceutical Sciences, a standard reference text in the field, which is incorporated herein by reference. Preferred examples of such carriers or diluents include, but are not limited to, water; saline; dextrose solution; human serum albumin; HBSS and other buffered solutions (including those with and without $Ca^{++}$ and $Mg^{++}$) known to those skilled in the relevant arts; and basal media. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions can be included in a container, pack, kit, or dispenser together with instructions for administration.

The dosage regimen is selected in accordance with a variety of factors including species, age, weight, sex, and medical condition of the patient; type and severity of the condition to be treated; the route of administration; and the particular cells employed. An ordinarily skilled physician or veterinarian can readily determine and prescribe the effective amount required to prevent, counter, or arrest the progress of the condition.

The cell preparation of the invention can be administered topically to the wound in need of treatment. The thrombin+ cell component (component #2) can be admixed with the fibrinogen component (component #1) before, during, or after application to the wound. In one embodiment, the components are applied to the wound site by simple pipetting or by co-extruding components from a tube or syringe applicator. Each components may also be applied in conjunction with a sterile gauze dressing. Moreover, those skilled in the art will recognize that the order of topical administration of the components can be varied (e.g. thrombin+cells component followed by fibrinogen component or fibrinogen component followed by thrombin+cells component).

The cell preparation of the invention can also be administered by spraying the components of the preparation onto the wound area. Spray pumps suitable for use in administering the cell preparation of the invention include those used for other medical applications, including nasal and throat sprays. Additionally, the cell preparation could be applied using a spray generated by compressed inert gasses rather than using a spray pump. For example, small canisters of medical grade inert gasses such as air and/or nitrogen can be used. The pressure of the gas can be used to propel fluids through a small orifice, thereby generating a fine mist spray. The pressure can act directly on the fluid or a pressure drop can pull fluid out into an air stream, which eventually would become a spray.

In another embodiment, the cell preparation of the invention may be spray administered as a two component product that is applied to a chronic ulcer in a sequential, two-step process. In this embodiment, the first component is a suspension of fibrinogen in HBSS (without $Ca^{++}$ and $Mg^{++}$) and the second component is a mixture of cells (including fibroblasts and keratinocytes), thrombin and cryoprotectants in HBSS (with $Ca^{++}$ and $Mg^{++}$). In this embodiment, the two components of the cell preparation are mixed together on the target wound area. Both components are applied to the chronic ulcer or wound using a spray applicator, such as a spray pump. For example, a spray pump may be used to deliver precise doses of both components during treatment of an ulcer or wound. The actual design of the spray pump used may vary depending on the manufacturer. Examples of suitable spray pumps include for example nasal and throat spray. The spray pump is manufactured of a material that can be sterilized using conventional techniques to avoid contamination of either component of the cell preparation.

Sprayed doses can range from about 50 µl to about 150 µl per spray, preferably from about 100 µl to about 150 µl per spray, most preferably about 130 µl per spray. To allow for concentrated application and for more precise delivery of the product, the spray pump should have a spray actuator mechanism that produces a narrow spray diameter rather than a large diameter spray. The spray actuator mechanism is the "arm" that orients and generates the spray via the orifice size. The area of the chronic ulcer or wound surface area covered by each spray depends directly on the distance of the actuator from the target. For example, the closer the spray actuator mechanism is to the target area, the smaller the surface area covered per spray. Likewise, the further away from the target area the spray actuator mechanism is, the larger the surface area covered per spray.

Preferably, the surface area covered ranges from about 11 $cm^2$ to about 14 $cm^2$. In one preferred embodiment, the distance between the spray nozzle and the target is approximately 6 cm. At this distance, using a narrow diameter spray actuator mechanism, one spray will cover a wound surface area of approximately 12.6 $cm^2$.

The number of cells landing on the target area of the patient (i.e., the number of cells per $cm^2$ of patient) will vary depending on the concentration of each of the components and the ratios of keratinocytes to fibroblasts used in component #2. Those skilled in the art will recognize that the concentration of cell in the second component of the cell preparation can be varied from about $1\times10^3$ cells/µl to about $50\times10^3$ cells/µl. For example, in some embodiments, the number of cells/µl of the cell preparation component #2 can range from about $5\times10^3$ cells/µl to about $20\times10^3$ cells/µl. Thus, if two sprays of approximately 130 µl/spray are administered to a patient, approximately about $1.3\times10^6$ to about $5.2\times10^6$ cells are administered to the patient.

Typically, the first component (fibrinogen) is sprayed onto the target followed by spraying the second component (thrombin+cells). The order of spraying of the components can be reversed. However, it is preferable to first apply the fibrinogen component and then subsequently apply the thrombin+cells component, which may optionally contain a cryoprotectant. Once the cells+thrombin component is sprayed onto the fibrinogen component, the two components will begin to gel, cure or polymerize almost immediately, allowing an equal distribution of cells on the target area. When the cells+thrombin component is applied first followed by the fibrinogen component, the resulting lag time allows the cells to migrate on the wound site due to the effects of gravity, which might cause the cells+thrombin component to "run" or "drip" after application, depending on the volume applied. This, in turn, could potentially lead to an unequal distribution of cells upon application of the fibrinogen component. Since the subsequent application of the fibrinogen component leads to polymerization, this could result in the formation of an uneven cell preparation.

In another embodiment, the cell preparation components can be administered as a spray that is mixed in the air prior to reaching the target area. In such an embodiment, two separate components could be sprayed at the same time using one or two spray actuator mechanisms. The spray mists of each component would then combine in the air, thereby initiating polymerization before the cell preparation reaches the target area (i.e., the wound site). This embodiment would make the cell preparation of the invention easier to apply, as it requires a single spray to apply the cells and to initiate fibrin polymerization.

Cryopreservation

In some embodiments, component #2 cells may be cryopreserved prior to use in the cell preparation of the invention. In such embodiments, component #2 contains cells+thrombin+a cryoprotectant. Those skilled in the art will recognize that, the terms "cryoprotectant" and "cryopreservant" are used interchangeably herein and cover agents used to achieve cryopreservation. Suitable cryoprotectants include, e.g. glycerol, ethylene glycol, and dimethyl sulfoxide ("DMSO"). In various embodiments, the cryoprotectant includes, but is not limited to a 10% glycerol solution, a 15% glycerol solution, and a 15% glycerol and 5% human serum albumin (HSA) solution. Those skilled in the art will recognize that any other cryoprotectants and cryoprotectant concentrations known in the art may also be used.

The cryoprotectants used in the instant invention can be included in the buffers containing component #2 of the cell preparation. In this protocol, no extra proteins need to be added. Likewise, the cells are not frozen in biological media. By choosing a cryoprotectant with low or no toxicity, there is no need to wash away or otherwise remove the cryoprotectant from the cells prior to use. This allows direct application of the cell preparation after thawing.

Cryopreservation facilitates shipping and long-term storage of the components of the cell preparation of the invention. Cryopreserved cells (in component #2) are stored at a temperature ranging from about $-70°$ C. to about $-196°$ C. (if liquid nitrogen is used). For example, the cryopreserved cells may be stored in a $-80°$ C. freezer or in the vapor phase of liquid nitrogen at $-160°$ C.

In one preferred cryopreservation protocol, a vial containing the cell+thrombin+cryoprotectant mixture (component #2) is closed with a screw-on closure in a sterile manner. The closed vial is then packaged (hermetically sealed) inside a pouch fabricated of a material that can resist temperatures ranging from $-70°$ C. to $-196°$ C., which is the temperature found in the liquid nitrogen vapor phase. Other storage temperatures between $-120°$ C. and $-160°$ C. can be found in the liquid nitrogen vapor phase. Vials or pouches containing vials are then placed inside a controlled rate freezer employed for the freezing of biological cells and tissues in a special rack designed to be inserted inside the controlled rate freezer. Typically, the vials or pouches are stored upright and aligned in several rows, such that there is space between each row. The rows are aligned parallel to the flow of the liquid nitrogen vapor that passes through the chamber to cool the samples. The use of such pouches helps to prevent contamination of the components during freezing and thawing of component #2.

After loading the samples into the chamber, a freeze cycle is initiated, as follows:

1. Beginning at room temperature or 20° C., the chamber is cooled at $-2°$ C. per minute until 4° C.
2. The chamber is then held at 4° C. for 52 minutes to stabilize all samples at 4° C.
3. The chamber is then cooled at $-1°$ C. per minute until $-5°$ C.
4. The chamber is then cooled at $-3°$ C. per minute until $-12°$ C.
5. The chamber is then cooled at $-7.5°$ C. per minute until $-20°$ C.
6. The chamber is then held at $-20°$ C. for 15 minutes.
7. The chamber is then cooled at $-1°$ C. per minute until $-80°$ C.
8. The chamber is then held at $-80°$ C. for 60 minutes.

The pouches are then removed from the freezer and stored at either $-160°$ C. or $-80°$ C. until the time of use.

Those skilled in the art will recognize that the exact method used in the cooling cycle may be changed or improved upon as necessary. In general, it is well known that cells or tissues should be cooled at a rate ranging from about −0.2° C./minute to about −5° C./minute. Moreover, cooling rate ranges of about −0.5° C./minute to about −2° C./minute are optimal for most cases.

The cooling rate is especially critical as the temperature is lowered to the freezing point of the cryoprotectant solution used. In the preferred embodiment described herein, cooling is accelerated around the freezing point of the solution. This global, rapid drop in chamber temperature is intended to induce the phase change by generating a thermal instability that would induce ice seeding. It is desirable to control the seeding of the phase transition process in order to initiate the phase transition of all samples at the same time. Seeding of the phase transition process may be controlled by several methods, including: creation of a point thermal instability by either (1) touching a sample with a metal probe chilled in liquid nitrogen or (2) ejecting a cooled liquid (e.g. liquid nitrogen) at the sample. (See U.S. Pat. Nos. 6,347,525; 6,167,710; and 5,981,617, each of which are incorporated herein by reference). Those skilled in the art will recognize that other means of controlling the phase transition can also be used. For example, any available technique that creates an instability in the supercooled solution such as mechanical stimulation (e.g. a pulsed vibration) can be used.

In some embodiments, the cell preparation of the invention can be delivered as a kit contained in a single package made from an aluminum foil laminate pouch that resists low temperatures. Inside this outer pouch are two smaller pouches, the first with a vial containing component #1 (fibrinogen) and the second with a vial containing component #2 (cells+thrombin+cryoprotectant). Alternatively, vials for components #1 and #2 can be packaged together in a single pouch or case. These inner pouches are also made from a temperature resistant material. Examples of suitable materials for these pouches include, but are not limited to, an aluminum foil laminate pouch, coated paper, LDPE, Surlyn®, and a Kapton™ laminate pouch (Steripack, Ireland). Those skilled in the art will recognize that any other suitable material may also be used to make these pouches. The material used to manufacture the pouch should have a low seal initiation temperature, high barrier performance, and good chemical resistance. Moreover, it should be suitable for irradiation sterilization to avoid contamination of the cell preparation components. An example of the composition and typical properties of a suitable pouch are provided in Tables 3 and 4.

TABLE 3

| STRUCTURE | Thickness (micron) | Weight (gm/m$^2$) |
|---|---|---|
| Paper | — | 50 |
| Polyethylene | 13 | 12 |
| Aluminum Foil | 9 | 25 |
| Surlyn ® | — | 23 |

TABLE 4

| PROPERTY | UNITS | Value (typical) |
|---|---|---|
| Tensile Strength (MD) | KN/m$^2$ | >50.0 |
| Tensile Strength (CD) | KN/m$^2$ | >20.0 |
| Elongation (MD) | % | >1.0 |
| Elongation (CD) | % | >2.0 |

TABLE 4-continued

| PROPERTY | UNITS | Value (typical) |
|---|---|---|
| Lamination Strength | T: 140° C., P: 4 bar, t: 0.3 sec | >5.0 |
| Water Vapor Transmission Rate | g/m$^2$ · d @ 38° C., 90% R.H. | <0.5 |
| Oxygen (O$_2$) Transfer Rate | cc/m$^2$ · d · atm@ 23° C., 50% R.H. | <2.0 |

The sealing parameters for a suitable pouch will depend on the particular sealing equipment used and its compatibility with the sealant layer of the secondary substrate. However, typical parameters for sealing can include: temperature=100-140° C.; dwell time=0.30-0.75 sec; and pressure-60-80 psi.

Figure 6A:
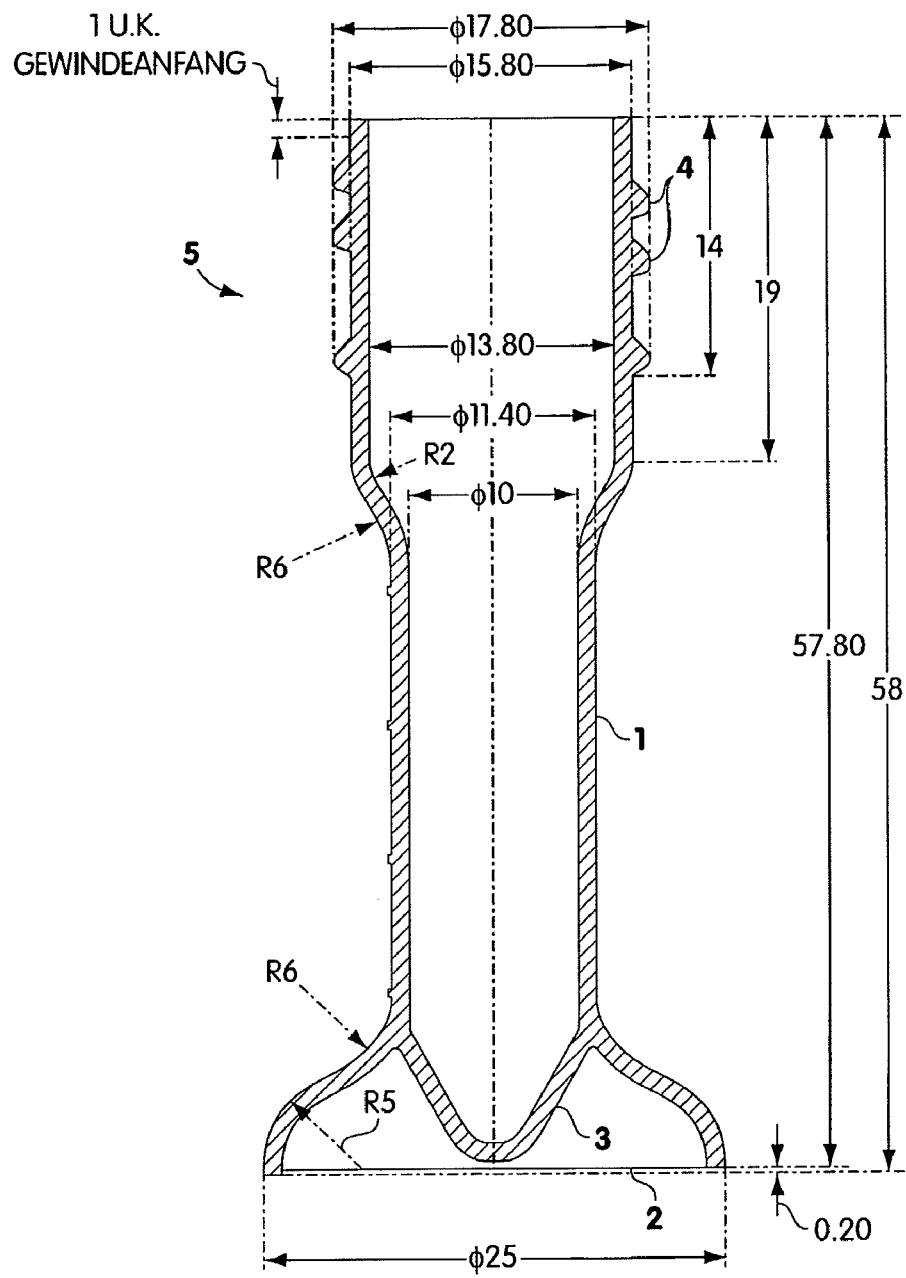
FIGS. 6a and 6b are pictures of a novel vial used for delivering and administering the cell preparation of the invention.
Figure 6B:
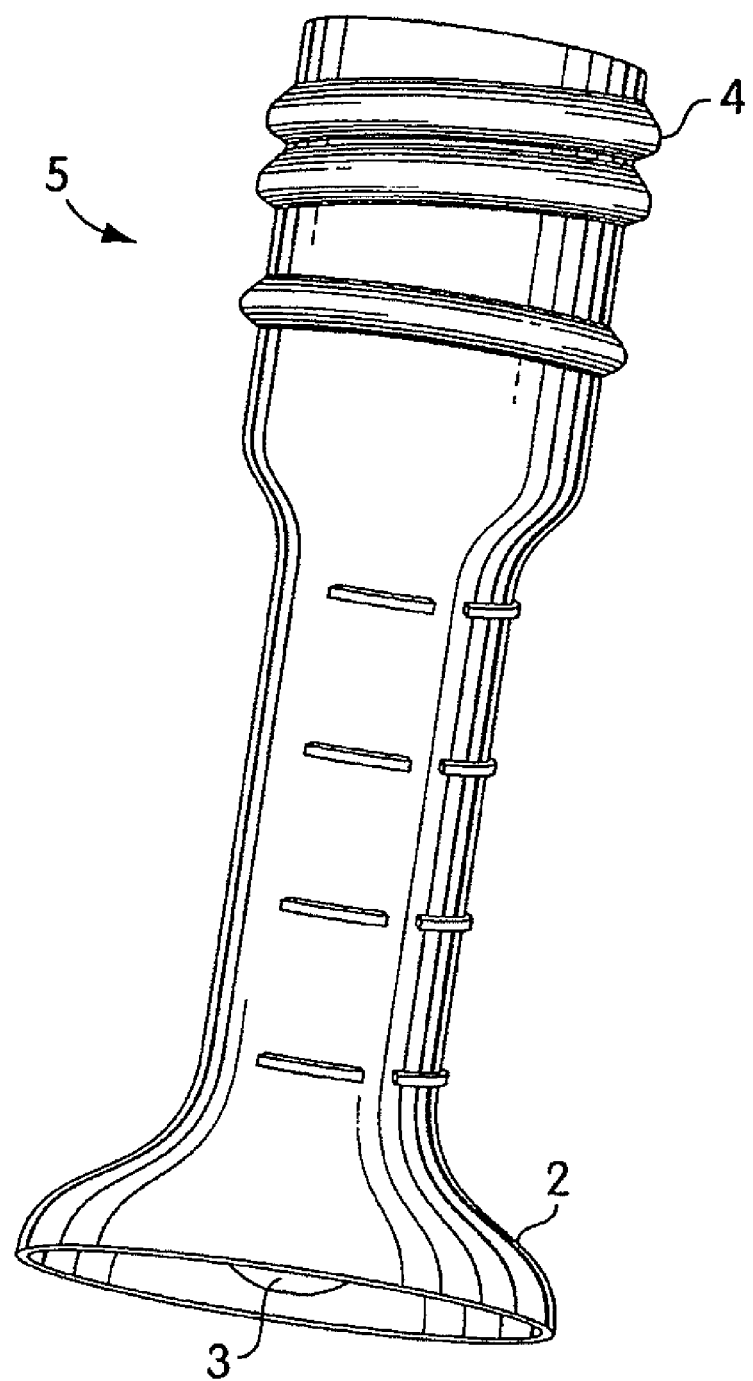

In another embodiment, the vials may be sealed in a rigid, transparent container, fabricated by using a polymer resistant to temperatures below −70° C. to as low as −196° C. A variety of different types of vials may be used for freezing components #1 and #2. In one preferred embodiment, a novel vial (5) such as that shown in FIG. 6a and FIG. 6b is employed. This vial is used to freeze down the components of the cell preparation of the invention. Upon thawing, the screw-on cap (4) closing the vial can be replaced with a spray pump applicator. In one embodiment, bottle may be made of polypropylene, which is resistant to the low temperatures employed in the cryopreservation protocol. The wall thickness of this vial (1) should be approximately 0.8 mm to facilitate heat/cold transfer across the wall, which is important for both the freezing and thawing processes. Additionally, the vial can be designed to stand upright after a spray pump has been screwed on, and the bottom of the vial (2) is conical (3) to facilitate emptying of the contents.

One spray pump designed to be used with this type of vial is manufactured by the company Valois. Each spray delivers a 130 μl volume of product. The spray actuator, which is the "arm" that orients and generates the spray via the orifice size, can be modified so that the "arm" can be oriented in directions other than the horizontal position, to aid in topical administration by allowing spray application onto a horizontal surface without tipping the bottle. In another embodiment, other spray pump designs can be employed which allow the spray to function when the bottle is inverted.

The cryopreserved components of the cell preparation of the invention can be shipped, stored, and/or used as follows. The components may be shipped as a kit frozen on dry ice at a temperature of about −70° C. to about −80° C. The pump may be shipped at room temperature. Upon arrival, the kit should be stored in a −80° C. freezer or at −160° C. until use. To use, the outer pouch of the kit is opened and the two smaller pouches containing component #1 (fibrinogen) and #2 (cells+thrombin+cryoprotectant) are removed and thawed in a water bath that is warmed to a maximum of 37° C. Those skilled in the art will recognize that the pouches serve to prevent water in the water bath from contaminating the components of the cell preparation. Once the contents of the vials are thawed, the pouches can be removed from the water bath, disinfected (if desired), and opened. The screw-on top from each vial is then removed and replaced with a screw-on spray applicator, and the cell preparation components are then ready for patient application.

The invention will be further described in the following examples, which do not limit the scope of the invention described in the claims.

Example 1

Isolation of Keratinocytes and Fibroblasts

Keratinocytes and fibroblasts may be isolated after splitting the epidermis from the dermis using an enzyme such as dispase or thermolysin. The isolated epidermis can be incubated with trypsin to obtain a single cell suspension of keratinocytes, which can then be plated onto culture dishes and amplified to create a bank of primary keratinocytes. The isolated dermis can be incubated with a dissociation enzyme such as collagenase to obtain fibroblast single cell suspensions ready to be plated and amplified or minced and dispatched onto a culture plate, and cultured until fibroblasts have migrated from the tissue. These cells can then be collected after trypsin treatment and further amplified to establish a fibroblast cell bank. Primary human keratinocytes and fibroblasts isolated in this manner can be used for the preparation of cell and fibrin admixtures.

The isolation of fibroblasts may also be carried out as follows: fresh tissue samples are thoroughly washed and minced in Hank's balanced salt solution (HBSS) in order to remove serum. The minced tissue is incubated from 1 to 12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, and serially cultured or stored frozen in liquid nitrogen (see, Naughton et al., 1987, J. Med. 18(3&4):219-250). Fibroblasts or subpopulations of fibroblasts such as dermal papilla cells or myofibroblasts can be isolated from explant outgrowth culture. Once isolated, the stromal cells are ready for admixture with an extracellular matrix (e.g. fibrin) paste.

Example 2

Composition of the Components of the Cell Preparation of the Invention

Component #1

This component can be made by performing a four-fold dilution of the Sealer Protein Solution in the Tisseel VH Fibrin Sealant (Baxter). After dilution, the concentration of the components in the Sealer Protein Solution was as follows:

| Fibrinogen: | 18.75 mg/ml-28.75 mg/ml |
| --- | --- |
| Fibrinolysis Inhibitor (Aprotinin): | 750 KIU/ml |
| Polysorbate: | 0.05 mg/ml-0.1 mg/ml |
| Sodium Chloride: | 0.5 mg/ml-1.0 mg/ml |
| Trisodium Citrate: | 1.0 mg/ml-2.0 mg/ml |
| Glycine: | 3.75 mg/ml-8.75 mg/ml |

The Sealer Protein Solution was diluted in Hank's Buffered Saline Solution (HBSS) without $Ca^{2+}$ or $Mg^{2+}$. The presence of these two ions induced the formation of precipitates during the freezing and thawing process.

Those skilled in the art will recognize that the Tisseel Sealant can be supplemented with other commercially available fibrinogen and aprotinin preparations to achieve similar results. Moreover, fibrinogen may also be diluted to other concentrations, depending on the mode of administration, to enhance the polymerization characteristics.

Component #2

This cryoprotected component can be made by mixing the following:

| Components | Final Concentration |
| --- | --- |
| Thrombin (Baxter Tisseel): | 10% by volume |
| Glycerol | 15% by volume |
| Human Serum Albumin | 5% by volume |
| HBSS (with $Ca^{2+}$ and $Mg^{2+}$) | Used to resuspend these components |

Following dilution, the thrombin solution obtained from Baxter contributes the following to the cryoprotected solution:

| Thrombin: | 50 IU/ml |
| --- | --- |
| Total protein: | 4.5-5.5 mg/ml |
| Sodium Chloride: | 0.8-1.2 mg/ml |
| Glycine: | 0.24-0.36 mg/ml |
| $CaCl_2$: | 4 µmol |

HBSS with $Ca^{2+}$ and $Mg^{2+}$ was the chosen diluent.

The desired cell mixture (ratio) and concentration was resuspended in the cryoprotected solution to obtain the component #2. Various keratinocyte:fibroblast ratios have been considered, including 1:1, 1:3, 1:4, 1:9, to as high as 1:50. Moreover, various final cell concentrations in component #2 considered have been 1 million, 2.5 million, 5 million, 10 million, 20 million, and 50 million cells/ml (final concentration).

Example 3

Testing the Effective Dose of Mitomycin C

Previous work has shown the efficient concentrations of mitomycin C (MMC) for growth-arrest of mouse 3T3 fibroblasts to be 2 µg/ml (Rheinwald and Green, *Cell* 6:331-43 (1975)) and for growth arrest of human dermal fibroblasts to be 8 µg/ml (Limat et al., J. Invest. Dermatol. 92:758-62 (1989)).

The rat fibroblast cell line (CRL 1213), the FGF 1-transfected rat fibroblast cell line (1175/CRL 1213), the human telomerase immortalized fibroblast line (MDX12), and the primary human fibroblasts (EDX1) were each growth arrested using the following method. Fibroblasts were grown in DMEM+10% FCS, 25 mM Hepes, 1 mM pyruvate, 2 mM L-Gln, U/ml penicillin, 100 µg/ml streptomycin in T75 flasks. At confluency, the cells were detached and plated at a density of $10^5$ cells/cm$^2$, further incubated for 48 h, then treated with mitomycin C (MMC) at 0, 2, 4, 8, 12 µg/ml for 5 h. The cells were then rinsed with PBS and detached with 0.05% trypsin/0.02% EDTA. The remaining cells were plated at densities of 100 to 5000 cells/cm$^2$ in T25-flasks respectively (10 flasks for each density). These cells were incubated at 37° C. with 2 media changes per week.

Efficiency of cell growth arrest was measured by weekly counting of cells (using a hemacytometer) cultured in the flasks plated at a density of 5000 cells/cm$^2$ and by inspection of appearing colonies in the flasks plated at a density of 100 cells/cm². Changes in cell morphology were also examined. A concentration of 8 μg/ml MMC was sufficient to growth arrest the human primary fibroblasts (EDX1) and the hTERT immortalized human fibroblast line (MDX12) agreeing with previous data (Limat et al., J. Invest. Dermatol. 92:758-62 (1989)). The rat fibroblast line (CRL 1213) showed a toxicity to MMC-concentrations above 4 μg/ml, while 2 μg/ml MMC proved to be optimal to growth arrest these cells. The rat fibroblast cell line (1175/CRL 1213) transfected with the FGF1-gene, was growth arrested at a concentration of 1 μg/ml MMC. Concentrations below 1 μg/ml were not efficacious and higher concentrations of MMC were progressively toxic. Mitomycin C-treated fibroblasts (with the appropriate mitomycin-C dose), recovered from cryogenic storage by thawing, displayed a cell recovery of at least 50% (in agreement with Limat et al., In Vitro Cell Dev. Biol. 26:709-12 (1990)).

Example 4

Testing Effective Dose of Gamma Irradiation on Fibroblasts and Keratinocytes

To measure the effect of gamma (γ) irradiation on the mitotic activity of treated fibroblasts, a BrdU cell proliferation assay was employed which functions in a 96 well format (Oncogene Research Products). Non-immortalized, human primary fibroblast cells were treated with γ irradiation at various doses, including 0, 60, 70, and 80 Grays. Cells were then plated at a density of 5,000 cells per well in a 96 well dish. Irradiated and non-irradiated controls were maintained in culture for periods lasting 15 and 30 days. At each of these time points, the mitotic activity was measured using a BrdU incorporation assay in which BrdU incorporation in the DNA is assayed immunochemically and measured via its absorbance at 450 nm.

In FIG. 1, non-irradiated cells treated with BrdU served as a positive control for each experiment. Non-irradiated cells that were not treated with BrdU served as the background absorbance, which was subtracted from the absorbance at 450 nm for each sample (0, 60, 70, and 80 Grays) and the final data was normalized by setting the positive control to 100% relative BrdU incorporation. In FIG. 1, it is clear that treatment with γ irradiation at levels of 60 Grays and above induces primary fibroblasts into a post mitotic state. A total of 3 samples was considered for each condition. Data is shown as the average±SEM.

Figure 2:
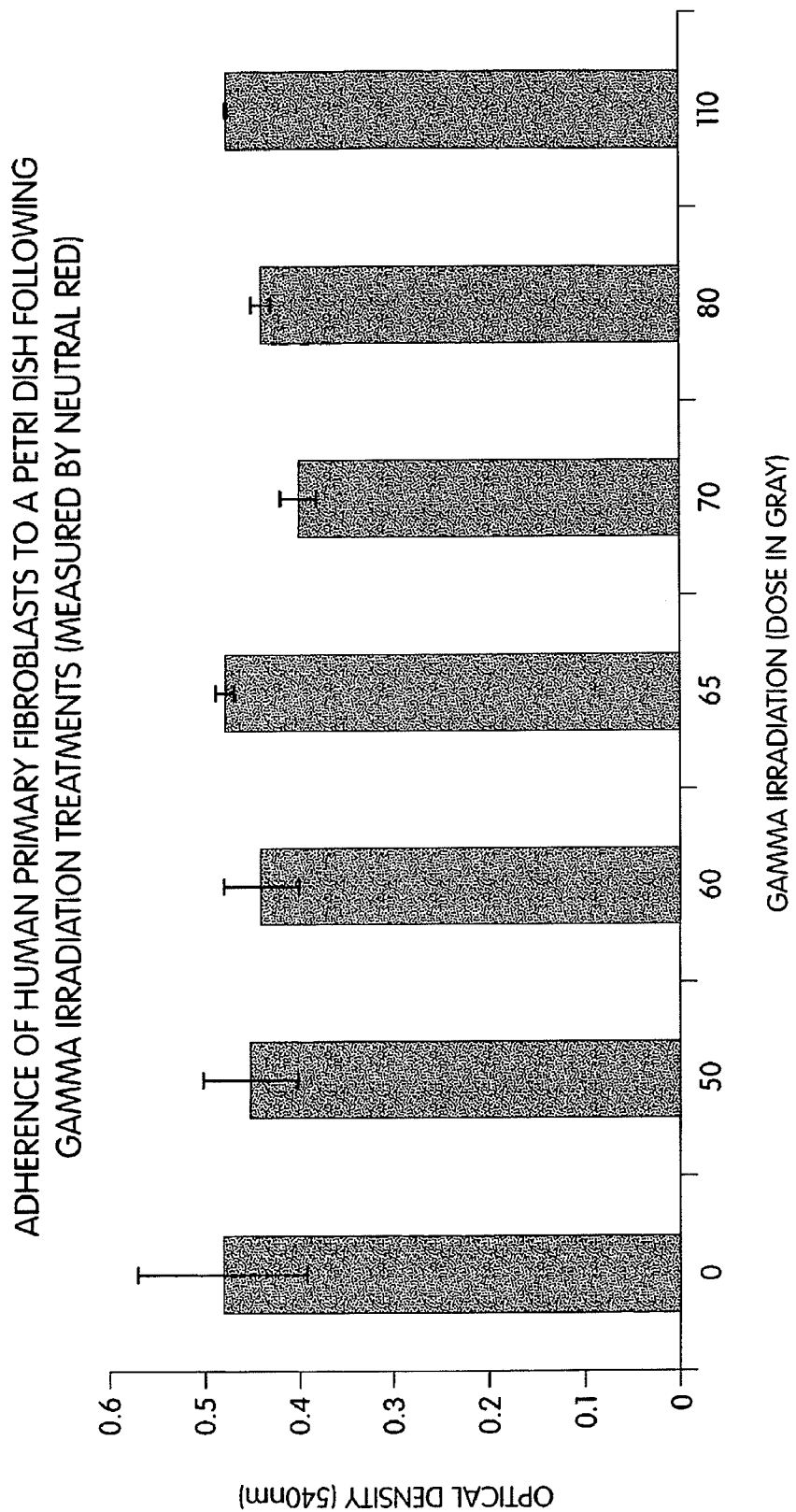
FIG. 2 is a histogram showing adherence of human primary fibroblasts to a petri dish following gamma irradiation treatments.

In FIG. 2, viability of cells following gamma (γ) irradiation treatment was assessed by determining the adhesion of cells to normal cell culture surfaces. Cells were plated in 6 well culture dishes at a concentration of 9,500 cells/cm² or 95,000 cells per well. Four hours after plating cells, media was replaced with a fresh media containing 50 μg/ml of Neutral Red and cells were incubated for 2 hours at 37° C. and 5% $CO_2$. Wells were then rinsed twice with NaCl 0.9% and dried overnight. The following day, the dye was dissolved using a mix of 1:1 acidic acid (2%) and ethanol (95%). Each well was incubated in 1 ml of this solution at room temperature for 15 minutes after which 200 ul of the mix was measured for its dye content at 540 nm. No significant difference was observed between the adherence of treated versus non-treated cells indicating that gamma (γ) irradiation does not effect cell viability and that cells may attached to a culture surface following gamma (γ) irradiation. Each data point is the average measurement of three separate 6 wells. Data is displayed as the average±SD.

Gamma (γ) irradiation at 80 Gy was also evaluated for its ability to induce differentiation of primary human keratinocytes into a post mitotic state. Irradiated keratinocytes were plated on a layer of growth arrested fibroblasts feeder cells (gamma (γ) irradiated at 70 Gy). Feeder cells were plated at a density of 5,000 cells/cm² and keratinocytes 12,500 cells/cm². Keratinocyte growth and phenotype were followed for 3 weeks thereafter by observation using an inverted microscope. During this period, keratinocytes were observed to adopt a differentiated phenotype, with cells increasing their size and area of attachment. Keratinocytes cultured in this manner were not able to divide and cover the culture surface, but instead remained either isolated or in small clusters, indicating that irradiation had induced cells into a post mitotic state.

Example 5

Testing Cell Densities with Fibrin Paste: Secretion of Growth Factors and Cytokines by Mixtures of Keratinocytes and Fibroblasts in a Fibrin Matrix Human primary keratinocytes and fibroblasts were growth arrested by gamma (γ) irradiation at 80Gy prior to formulation. Fresh preparations of human primary keratinocytes and fibroblasts were mixed at a ratio of 1:9 at final concentrations including 2.5, 5, 10, 20 and 40 million cells/ml in a suspension containing 10% thrombin (Tisseel, Baxter)+15% glycerol+5% Human serum albumin. In a second vial, a 25% fibrinogen (Tisseel, Baxter) solution was prepared. A cell and fibrin "paste" was prepared in individual wells of a 24 well plate by spraying together 1 spray (130 μl) of the cell+thrombin suspension with 1 spray (130 μl) of the fibrinogen suspension. Secretion of various growth factors and cytokines by these cells into media was measured during day 2 following preparation of the cells in the fibrin matrix. Data shown in Table 5 represents an average of 5 individual data points (samples) for each condition presented.

TABLE 5

| Cell Concentration | GM-CSF (pg) | | VEGF (pg) | | KGF (pg) | | HGF (pg) | | IL-1 beta (pg) | |
|---|---|---|---|---|---|---|---|---|---|---|
| | Average | SEM | Average | SEM | Average | SEM | Average | SEM | Average | SEM |
| 2.5 million/ml | 9 | 5 | 1002 | 80 | 90 | 6 | 1869 | 144 | 29 | 4 |
| 5 million/ml | 42 | 14 | 3528 | 385 | 207 | 9 | 3533 | 417 | 58 | 6 |
| 10 million/ml | 373 | 55 | 11739 | 822 | 332 | 15 | 5726 | 213 | 119 | 8 |
| 20 million/ml | 963 | 110 | 12637 | 1064 | 214 | 34 | 4956 | 563 | 276 | 51 |
| 40 million/ml | 602 | 82 | 4432 | 733 | 98 | 11 | 2140 | 197 | 927 | 45 |

Table 5 illustrates the variety of different growth factors are actively secreted from keratinocytes and fibroblasts contained in a fibrin matrix. It is also known in the art that bFGF produced by these cells can be found in the fibrin matrix. The absolute levels of growth factors produced were observed to be dependant on the particular nature of the growth factor in question. Because biological potency and half-life is molecule dependant, actual pg levels of independent growth factors is not the primary interest. Rather, it is believed that the biological action of the cocktail of molecules secreted from these cells together offers a unique way of targeting many biological pathways simultaneously. It is worth noting that physiological quantities of growth factors and cytokines are being produced.

In Table 5, the secretion of the 5 different molecules appears to be dose-dependant according to the cell concentration employed. This holds true as cell concentration increases from 2.5 to 10 million cells/ml. For most factors, except KGF and HGF, even higher secretion levels are witnessed at 20 million cells/ml. However, once the cell number increases to 40 million cell/ml, a drop in protein production is observed for all molecules except IL-1 beta. This suggests that an optimum cell concentration likely exists and that, as shown, each cell concentration will lead to the production of a different protein profile as seen in the Table 6 below. Table 6 was generated by normalizing the secretion of VEGF, KGF, HGF and IL-1 beta to that of GM-CSF. This illustrates that, for different cell concentrations, there exist a different protein profile, with molecules being produced at different ratios depending on the cell concentration under consideration.

TABLE 6

|   | GM-CSF | VEGF | KGF | HGF | IL-1 beta |
|---|---|---|---|---|---|
| 2.5 million/ml | 1 | 111.3 | 10 | 207.6 | 3.2 |
| 5 million/ml | 1 | 84 | 4.9 | 84.1 | 1.4 |
| 10 million/ml | 1 | 31.5 | 0.9 | 15.3 | 0.3 |
| 20 million/ml | 1 | 13.1 | 0.2 | 5.1 | 0.3 |
| 40 million/ml | 1 | 7.4 | 0.2 | 3.6 | 1.5 |

Example 6

Allox Phase I Clinical Trial C2001

Product Description

The allogeneic cell-based treatment (named Allox) under investigation is a two component product which can be applied topically to chronic ulcers using a spray applicator. Upon spraying the two components on the wound site, a fibrin matrix is created that traps the applied cells at the region of the ulcer, permitting local release of trophic factors by these cells.

The contents of the 2 components were:

| | |
|---|---|
| Component #1 | A liquid suspension of fibrinogen; (1 spray = 50 µl) |
| Component #2 | A liquid suspension of keratinocytes and fibroblasts (Ratio 1:1, 15 × $10^6$ cells/ml) mixed with thrombin; (1 spray = 50 µl) |

Objective

The objective of this study was to assess the effects Allox on the wound healing of chronic ulcers, to assess its safety and tolerability in a patient population, and to determine the effect of the product on the incidence of complete wound closure of chronic leg ulcers in patients with venous or arteriovenous insufficiency.

Methodology

Patients over 18 years of age with at least one venous or combined arterio-venous ulcer between the ankle and the knee who met the protocol's eligibility criteria were recruited to receive Allox in the C2001 study. At study day (SD)—14, patients were found eligible and recruited to receive the Allox treatment. At SD1, patients received the first application of the study treatment, which was repeated on a weekly basis up to 8 weeks, or until ulcer closure, whichever came first. A follow-up visit occurred 4 weeks following the last application of the treatment.

Patient Number

A total of 13 patients were initially enrolled, one of whom was determined to be not eligible for the protocol at a later time.

Diagnosis and Main Criteria for Inclusion

Patients over 18 years of age with one or more venous or combined arterio-venous ulcers between the ankle and the knee whose etiology was confirmed by Ankle Brachial Pressure Index, by Ankle and/or Great Toe pressure, and by Duplex Ultrasound were eligible for this study. At SD—14 patients had to have an ulcer longer than 1 month duration with a surface area greater than 1 $cm^2$. Patients were required to be capable of communicating and cooperating with the Investigator and other staff and had to provide informed written consent. Female patients must have been post-menopausal or surgically sterilized.

Test Treatment and Mode of Administration

Application by sequential spraying of the solutions provided in the two bottle kit. A total 0.4 ml of product was applied alternatively: 2 sprays of component #1 (fibrinogen) followed by 2 sprays of component #2 (cells+thrombin). This procedure was repeated twice. Such an application covers 12 $cm^2$ of ulcer area, and each $cm^2$ of treated wound received a total of $0.25×10^6$ cells.

Duration of Treatment

At SD1, patients received the first application, which was repeated on a weekly basis up to 8 weeks, or until ulcer closure, whichever came first. A follow-up visit would occur 4 weeks following the last application. The study duration period was 14 weeks, consisting of a 2-week run-in period, an 8 week treatment and a follow up period of 4 weeks.

Criteria for Evaluation

Efficacy was assessed by noting complete closure of the ulcer; ulcer surface area at W8 and W12 compared to SD1; edge effect; and ulcer symptoms.

Safety was monitored by following the frequency and severity of adverse events until week 12. Standard laboratory tests, physical examinations and vital sign measurements were also recorded.

Statistical Methods

Given the small number of patients treated, no statistical analysis was performed. Rather, results are presented herein in descriptive form.

Results

TABLE 7

ULCER SURFACE REDUCTION IN INDIVIDUALS PATIENTS TREATED WITH ALLOX

| Patient ID | Center | Ulcer surface area (cm$^2$) at SD1 | Ulcer surface area (cm$^2$) at SD57 | Ulcer surface area (cm$^2$) at 4 Weeks Follow Up | % of area reduction SD1-SD57 | % of area reduction SD1-Follow Up |
|---|---|---|---|---|---|---|
| 200111 | 1 | 50.4 | 52.0 | 55.2 | −3 | −10 |
| 200113 | 1 | 14.0 | 15.4 | 12.5 | −10 | 10 |
| 200114 | 1 | 44.0 | 50.9 | 62.8 | −16 | −43 |
| 200124 | 2 | 21.5 | 20.4 | 19.9 | 5 | 7 |
| 200125 | 2 | 11.8 | 10.2 | 9.8 | 14 | 16 |
| 200126 | 2 | 7.7 | 16.2 | 16.2 | −110 | −110 |
| 200127 | 2 | 10.6 | 6.5 | 5.8 | 38 | 45 |
| 200129 | 2 | 64.5 | 72.6 | 73.5 | −13 | −14 |
| 200141 | 4 | 10.3 | 5.5 | 0.5 | 47 | 95 |
| 200142 | 4 | 20.0 | 14.0 | 10.3 | 30 | 48 |
| 200143 | 4 | 0.8 | 0.0 | 0.0 | 100 | 100 |
| 200144 | 4 | 1.8 | 0.1 | 0.0 | 92 | 100 |

A total closure was observed for one ulcer at SD57 and for two ulcers at the week 4 follow-up. For 5 patients, an improvement defined as more than 30% decrease in surface area was noted. Treatment failure, which was defined as either no reduction in ulcer size or an increase of ulcer size during the study period, was observed in 4 patients treated with Allox.

Clinical Study Conclusions

Weekly Allox treatments over an 8 week period were determined to be safe and non-toxic to patients with chronic leg ulcers. The two ulcer infections that were potentially treatment related resolved before the study end. Mild ulcer infections are relatively common place if correct hygiene is not respected.

Five patients showed greater than 30% reduction of area at the end of the follow up period, with 2 patients displaying complete ulcer closure. From this small study, a tendency towards response was observed in "younger" ulcers (<6 months).

Example 7

Testing Optimal Dilutions of Tisseel VH (Fibrin Glue) and Standard Human Plasma

Fibrin is one potential biological polymer that can be employed for suspending and trapping cell mixtures for therapeutic purposes. Polymerized fibrin is created by mixing fibrinogen and thrombin together at appropriate concentrations. In the matrix shown in FIG. 3, various dilutions of the fibrinogen (Tisseel, Baxter) and thrombin (Tisseel, Baxter) were tested for their effect on the polymerization process and generation of the end product fibrin. Dilutions considered ranged from ¼ to ⅛₀ of the original fibrinogen and thrombin components supplied in the TissuCol kit. In the original Tisseel kit, fibrinogen had a concentration of 75 to 115 mg/ml, while thrombin had a concentration of 500 IU/ml. For this study, the fibrinogen was diluted in HBSS without Ca$^{2+}$ and Mg$^+$ and the thrombin was diluted in HBSS with Ca$^{2+}$ and Mg$^{2+}$.

Fibrin characteristics considered included polymerization time (seconds), consistency, and mechanical strength. The fibrin polymer was generated using a spray technique by which one spray of fibrin was combined with one spray of thrombin in a single well of a 24 well culture plate. Conditions were repeated in triplicate. The spray volume employed was 130 μl per spray.

All dilutions considered permitted the formation of a fibrin polymer, though the properties of the fibrin polymer varied widely depending on the dilutions employed. The consistency and the mechanical strength of the fibrin were rated using the scale (−, +, ++, +++) in witch − was considered poor and +++ was considered excellent. Ratings of ++ or +++ were considered to be acceptable for potential use to suspend cells for therapeutic applications. The conditions for the maximal dilution of fibrinogen was ½₀ fibrinogen and ⅛ thrombin, while the conditions for the maximal dilution of thrombin was ¼ fibrinogen and ¹⁄₄₀ thrombin.

Additionally, normal plasma can also be used as a matrix material for the production of a biological glue to trap cells at the application site of a wound. Mixtures made by pipetting normal undiluted human plasma together with thrombin at a dilution of ¹⁄₅₀ permitted the formation of a fibrin clot or polymer. This fibrin polymer showed handling characteristics similar to the commercially available fibrin glues, suggesting that it can serve as a substitute to Baxter's Tisseel VH or Tissucol and Haemacure's APR concentrated fibrin-based products.

Example 8

Comparison of Growth Factor Release from Sprayed Versus Non-Sprayed Cells

Figure 4:
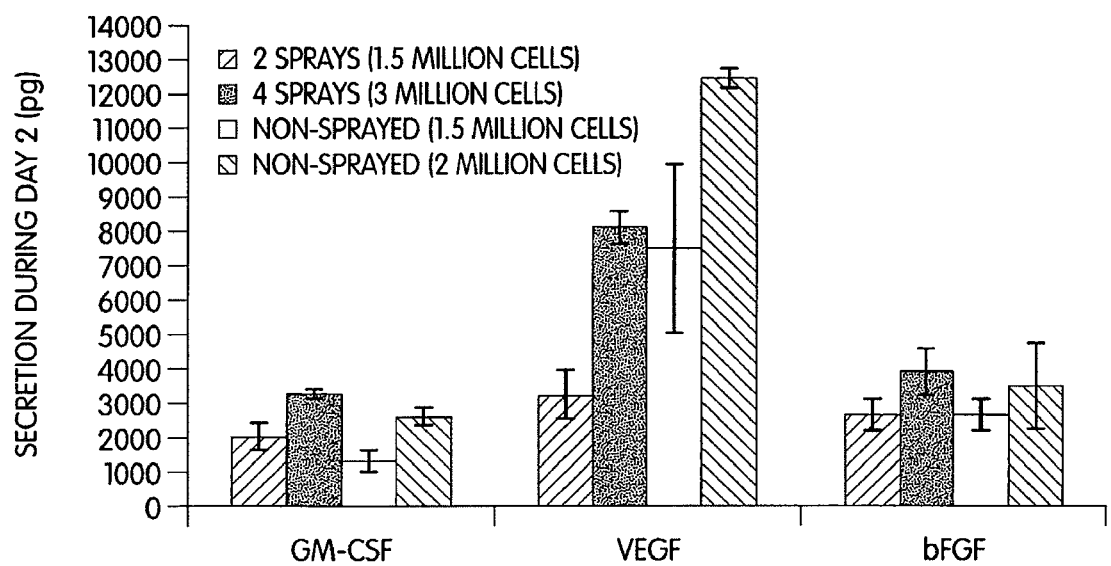
FIG. 4 is a histogram comparing the quantity of growth factors secreted by cell matrices when different doses of cells are sprayed into individual wells of a 24 well culture dish. The figure also shows growth factor secretion quantities when the fibrin matrix containing cells is prepared by simple pipetting (non-sprayed administration) of the fibrinogen and the thrombin+cell suspensions together.

FIG. 4 shows the secretion of growth factors from cells entrapped in a fibrin matrix, according to the methods of the instant invention. VEGF and GM-CSF secretion was assessed from medium conditioned for 24 hours during the second day following production of the fibrin cell matrix. bFGF secretion was measured in extracts obtained from the cell matrix 48 hours after production. To growth arrest cells, both primary human fibroblasts and keratinocytes were treated with 8 ug/ml mitomycin during five hours. Cells were rinsed with HBSS without Ca$^{2+}$ and Mg$^{2+}$ prior to trypsinization.

Cells were applied using a spray pump delivering 50 μl per spray.

Keratinocyte: Fibroblast Ratio=1.4

2 sprays (1.5×10$^6$ cells): 100 μl (15 million cells/ml) (cells+thrombin) component+100 μl fibrinogen component.

4 sprays (3×10$^6$ cells): 200 μl (15 million cells/ml) (cells+thrombin) component+200 μl fibrinogen component.

Non-sprayed (1.5×10$^6$ cells): 100 μl (15 million cells/ml) (cells+thrombin) component+100 μl fibrinogen component.

Keratinocyte:Fibroblast Ratio=1:1

Non-sprayed (pipetted) (2×10$^6$ cells): 250 μl (8 million cells/ml) (cells+thrombin) component+250 μl fibrinogen component.

FIG. 4 compares the quantity of secreted growth factors produced by cell and fibrin preparations following spray of different cell doses into individual wells of a 24 well culture dish. The figure also shows growth factor secretion quantities when cell and fibrin preparations are made by simple pipetting (non-sprayed). A comparison of sprayed versus non-sprayed preparations indicates that there is a decrease in measured VEGF secretion, while GM-CSF and bFGF secretion levels are comparable. Additionally, an increase from 2 to 4 sprays led to higher secretion levels of growth factors by the cells, which highlights the possibility of dosing growth factors by altering the number of cells. Secreted GM-CSF and VEGF were dosed in the culture media, while bFGF was dosed in the fibrin matrix. Data is presented as the average+SEM (n=4, spray; n=3, non-sprayed).

Example 9

Figure 5A:
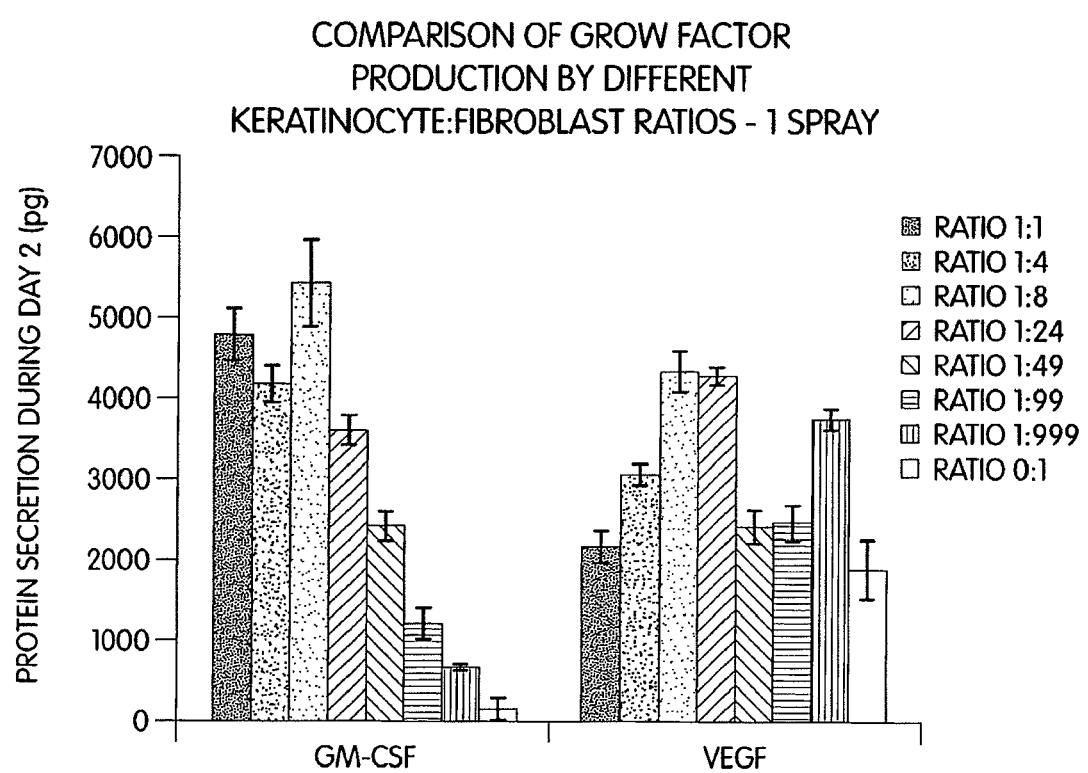
FIGS. 5a and 5b are histograms demonstrating that mixing sprayed keratinocytes and fibroblasts at different ratios, while maintaining a constant total number of cells, gives rise to variable growth factor secretion characteristics.
Figure 5B:
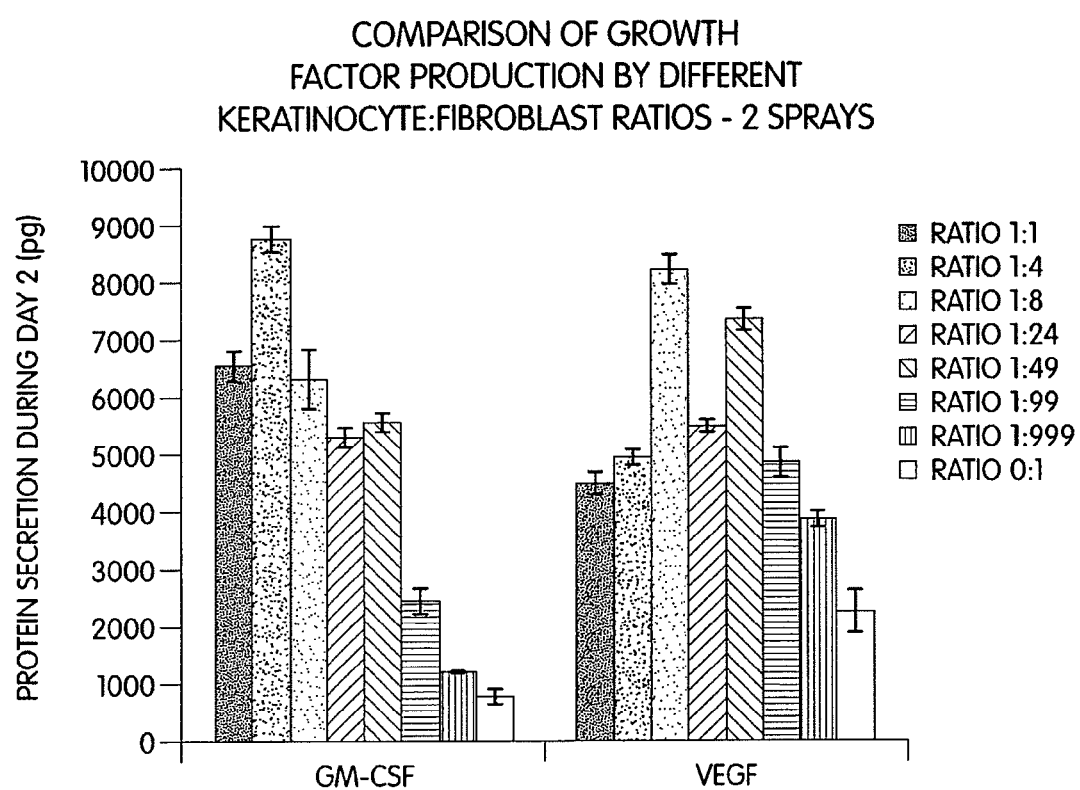

Comparison of Growth Factor Production by Different Keratinocyte:Fibroblast Cell Ratios In FIG. 5a and FIG. 5b, a comparison is made of growth factors released from cells entrapped in a fibrin matrix. The fibrin cell matrix is formed by spraying either one or two sprays of component #2 (cells+thrombin) with one or two sprays of component #1 (fibrinogen). A concentration of $15 \times 10^6$ cells/ml in component #2 was employed and the spray pump used delivered a volume of 70 µl per spray. To growth arrest cells, both primary human fibroblasts and keratinocytes were treated with 8 ug/ml mitomycin during 5 hours. Cells were rinsed with HBSS without $Ca^{2+}$ and $Mg^{2+}$ prior to trypsinization.

In FIG. 5a, one spray ($1.05 \times 10^6$ cells)=1 spray of cells+thrombin (70 µl) and 1 spray of fibrinogen (70 µl). In FIG. 7b, two sprays ($2.1 \times 10^6$ cells)=2 spray of cells+thrombin (140 µl) and 2 sprays of fibrinogen (140 µl).

FIGS. 5a and 5b demonstrate that mixing keratinocytes and fibroblasts at different ratios, while maintaining a constant total number of cells, gives rise to variable growth factor secretion characteristics. As keratinocytes are added to the fibroblasts, an increase in GM-CSF secretion is observed. For one spray, at keratinocytes:fibroblasts ratios of 1:24 to 1:8 a plateau is reached for GM-CSF production. Further addition of keratinocytes to the second component of the cell preparation of the invention does not appear to provide an advantage in terms of GM-CSF secretion.

Considering two spray preparations, at a keratinocytes:fibroblasts ratios of 1:49 to 1:1 the GM-CSF secretion passes 5000 pg/day. While GM-CSF secretion is highest at a keratinocyte:fibroblast ratio of 1:4, it is apparent that the largest increase in GM-CSF secretion is gained when passing from a ration of 1:99 to 1:49.

Moreover, it is also evident that VEGF production is highly dependant on the ratio of keratinocytes to fibroblasts in component #2. In the experiments detailed in FIGS. 5a and 5b, there appears to be optimal secretion of VEGF near a keratinocytes:fibroblasts ratio of 1:8, since further increasing the number of keratinocytes leads to a decrease in the quantity of VEGF secreted.

At different cell ratios, the application of a greater number of sprays also leads to an increase in growth factor secretion levels. Data is shown as average±SEM (n=4, 1 spray; n=3, 2 sprays).

Example 10

Comparison of Storage at −160° C. Versus −80° C. During One Week

Figure 7:
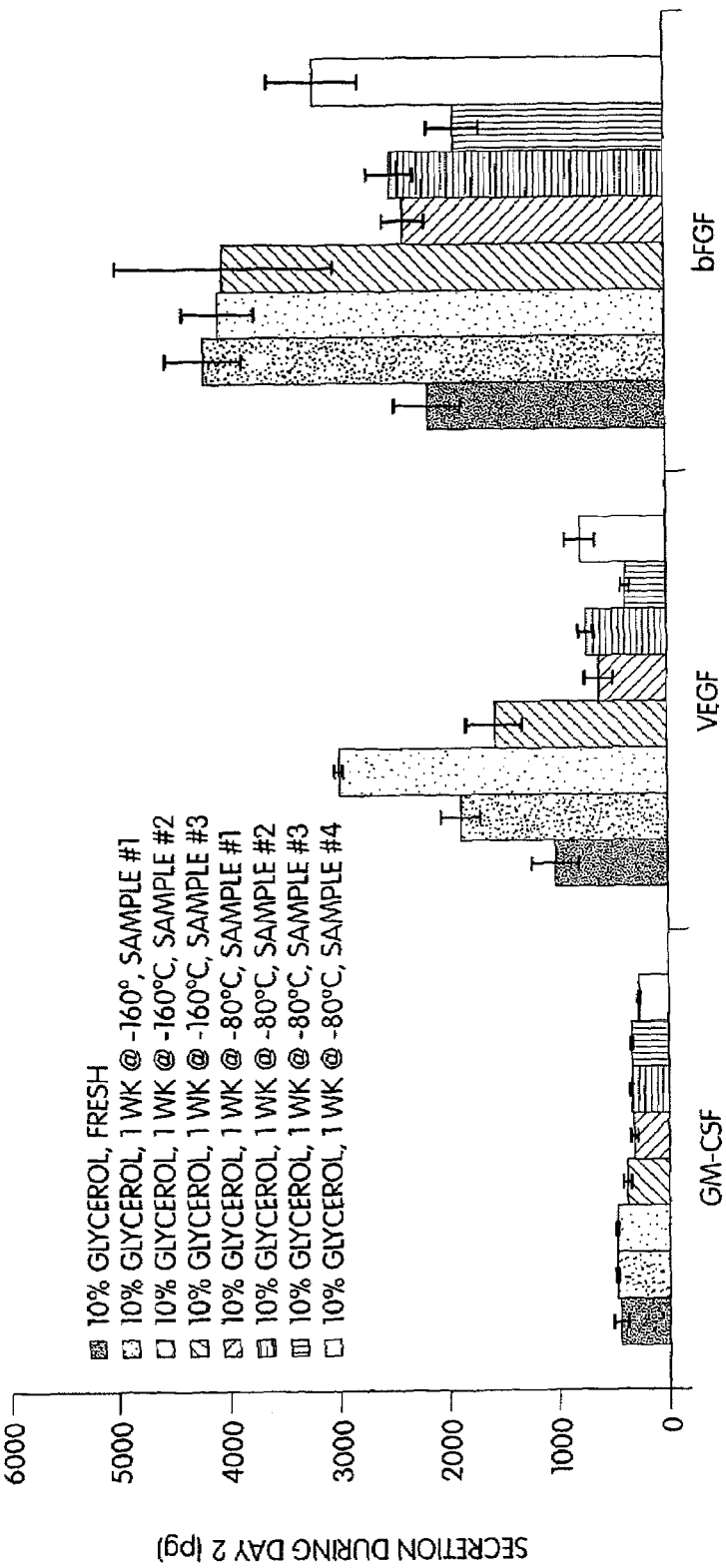
FIG. 7 is a histogram comparing growth factor secretion by cells stored for one week at −160° C. versus cells stored at −80° C. when using a 10% glycerol solution as a cryoprotectant.

FIG. 7 shows a comparison of growth factor secretion by cells stored cryopreserved at −160° C. versus at −80° C. for a period of one week. The cryoprotectant used in this experiment was a 10% glycerol solution with 10% thrombin (Tisseel, Baxter) and the keratinocyte:fibroblast ratio employed was 1:1. Prior to cryopreservation, cells were detached from their culture surfaces using trypsin and subsequently irradiated using gamma (γ) irradiation at 80Gy. A controlled rate freezer was used to gradually cool cell preparations to −80° C. After thawing one week later, one spray (130 µl) of the cell preparation (1.3 million cells at 10 million cells/ml) were spray mixed with one spray (130 µl) of fibrinogen in single wells of a 24 well petri dish. The results show GM-CSF, VEGF, and bFGF secretion during day 2 for three samples stored for one week at −160° C. and four samples stored for one week at −80° C. compared to a control fresh (unfrozen) sample containing the same cryoprotectant. Secreted GM-CSF and VEGF were dosed in the culture media, while bFGF was dosed in the fibrin matrix. Secretion data indicates that both −80° C. and −160° C. are suitable for storage, though −160° C. may be preferable when using a 10% glycerol solution. Data is shown as average±SEM (n=4).

Example 11

Figure 8:
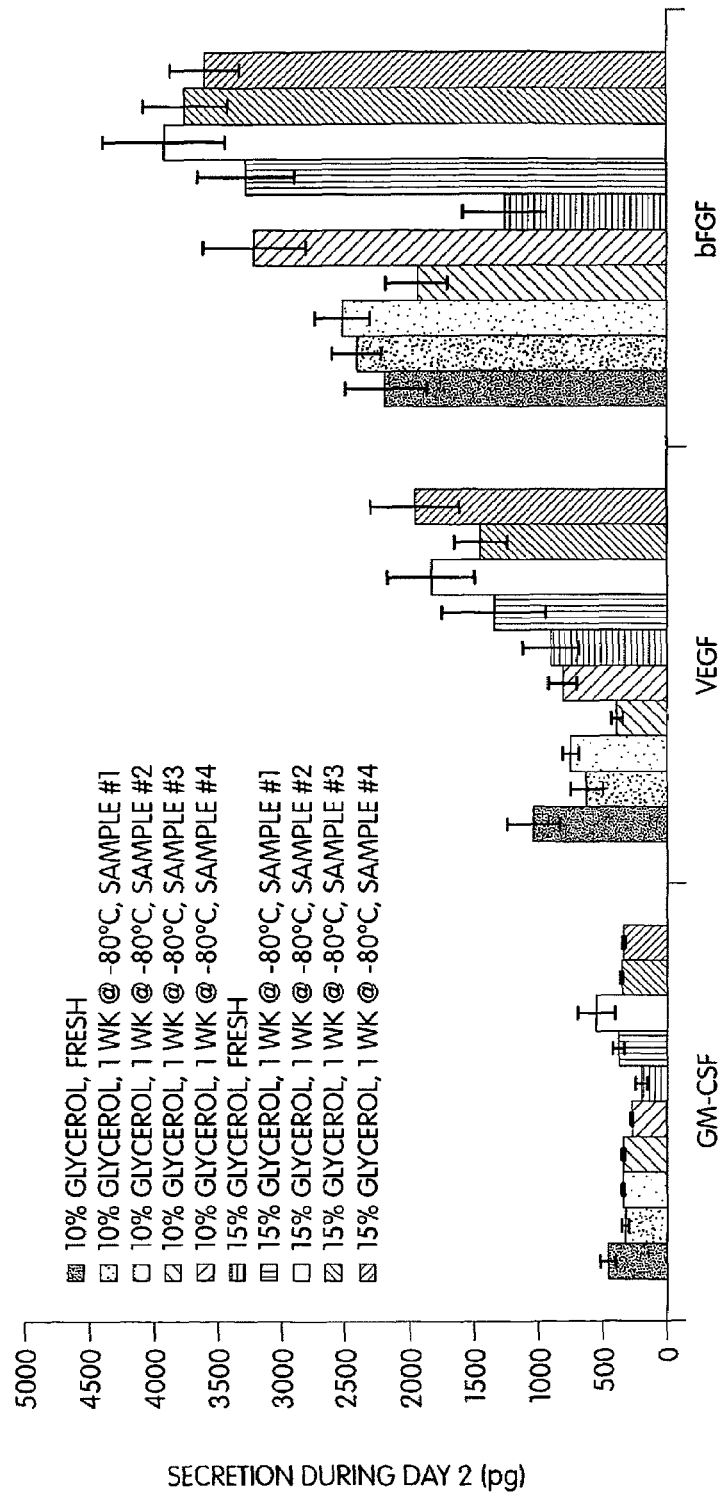
FIG. 8 is a histogram comparing growth factor secretion by cells stored for one week at −80° C. in 10% glycerol versus 15% glycerol.

Comparison of Secretion after One Week Storage at −80° C. in 10% Glycerol Versus 15% Glycerol FIG. 8 shows a comparison of GM-CSF, VEGF and bFGF secretion by cells cryopreserved at −80° C. in 10% glycerol versus in 15% glycerol for a period of one week. The keratinocyte:fibroblast ratio used in this example was 1:1 mixed with 10% thrombin (Tisseel, Baxter) and a cryoprotectant. Prior to cryopreservation, cells were detached from their culture surfaces using trypsin and subsequently irradiated using gamma (γ) irradiation at 80Gy. A controlled rate freezer was used to gradually cool cell preparations to −80° C. After thawing one week later, one spray (130 µl) of the cell preparation (1.3 million cells at 10 million cells/ml) were spray mixed with one spray (130 µl) of fibrinogen in single wells of a 24 well petri dish.

The results show GM-CSF, VEGF, and bFGF secretion during day 2 for four samples stored for one week at −80° C. using 10% glycerol and four samples stored for one week at −80° C. using 15% glycerol compared to control fresh (unfrozen) samples containing the same cryoprotectant concentrations. A trend of higher protein secretion was observed in samples stored in 15% glycerol versus those kept in 10% glycerol. Secreted GM-CSF and VEGF were dosed in the culture media while bFGF was dosed in the fibrin matrix. Data is presented as average±SEM (n=4).

Example 12

Figure 9:
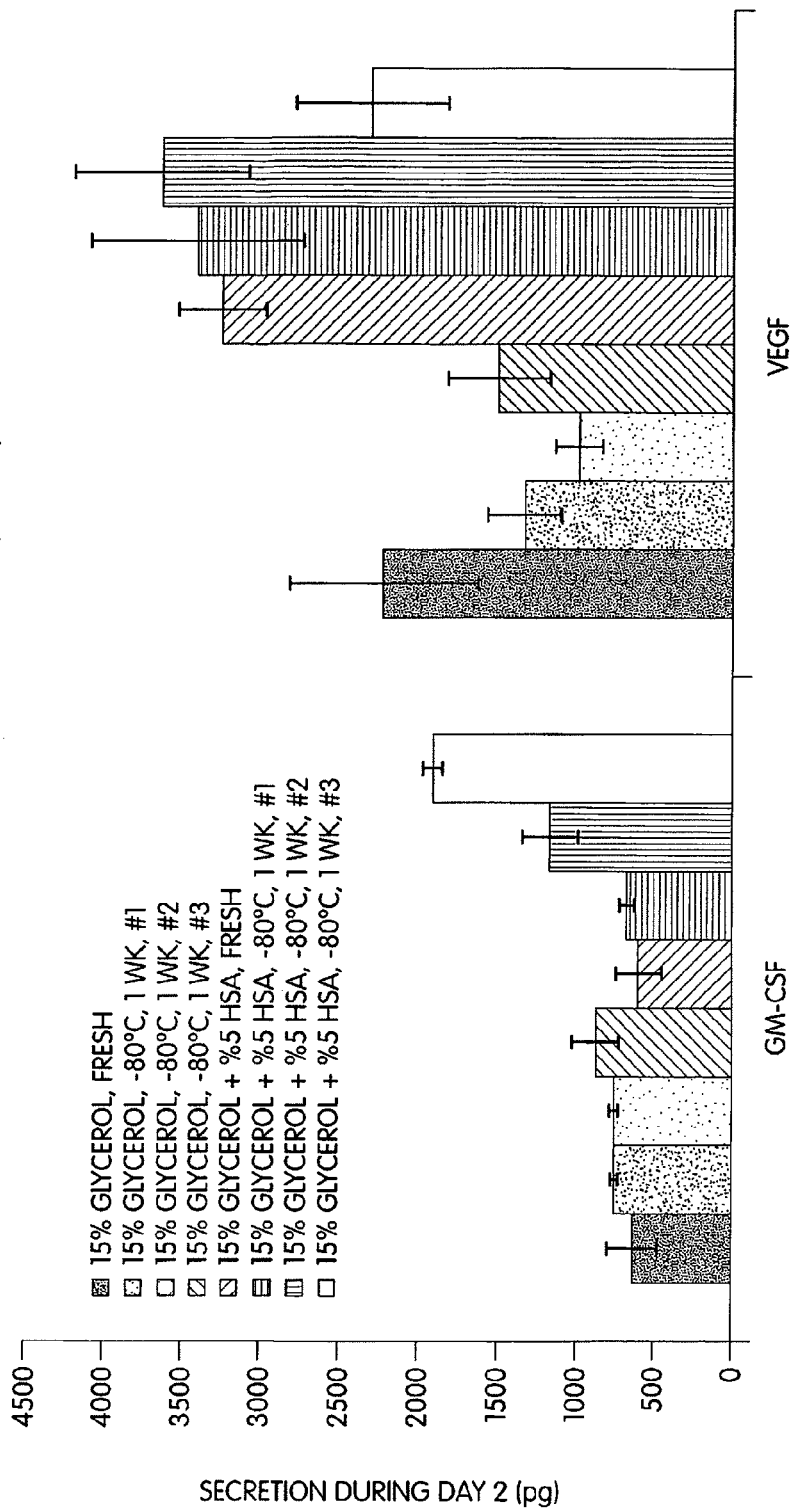
FIG. 9 is a histogram comparing growth factor secretion by cells stored for one week at −80° C. in 15% glycerol versus 15% glycerol+5% HSA.

Comparison of Secretion after One Week Storage at −80° C. in 15% Glycerol Versus 15% Glycerol+5% HSA FIG. 9 shows a comparison of growth factor secretion by cells cryopreserved at −80° C. in 15% glycerol versus 15% glycerol+5% Human Serum Albumin (HSA) (Griffols) for a period of one week. The keratinocyte:fibroblast ratio used in this example was 1:3 mixed with 10% thrombin (Tisseel, Baxter) and a cryoprotectant. Prior to cryopreservation, cells were detached from their culture surfaces using trypsin and subsequently irradiated using gamma (γ) irradiation at 80Gy. A controlled rate freezer was used to gradually cool cell preparations to −80° C. After thawing one week later, one spray (130l) of the cell preparation (1.3 million cells at 10 million cells/ml) were spray mixed with one spray (130 µl) of fibrinogen in single wells of a 24 well petri dish. The results show GM-CSF, VEGF, and bFGF secretion during day 2 for three samples stored for one week at −80° C. using 15% glycerol and three samples stored for one week at −80° C. using 15% glycerol+5% HSA (Griffols) compared to control fresh (unfrozen) samples containing the same cryoprotectants. Secretion data indicates that the addition of Human Serum Albumin improves the frozen product formulation by permitting higher protein secretion levels. Data is presented as average±SEM (n=4).

Example 13

Bioactivity of Keratinocyte and Fibroblast Mixtures Following Long-Term Storage at 80° C.

Figure 10:
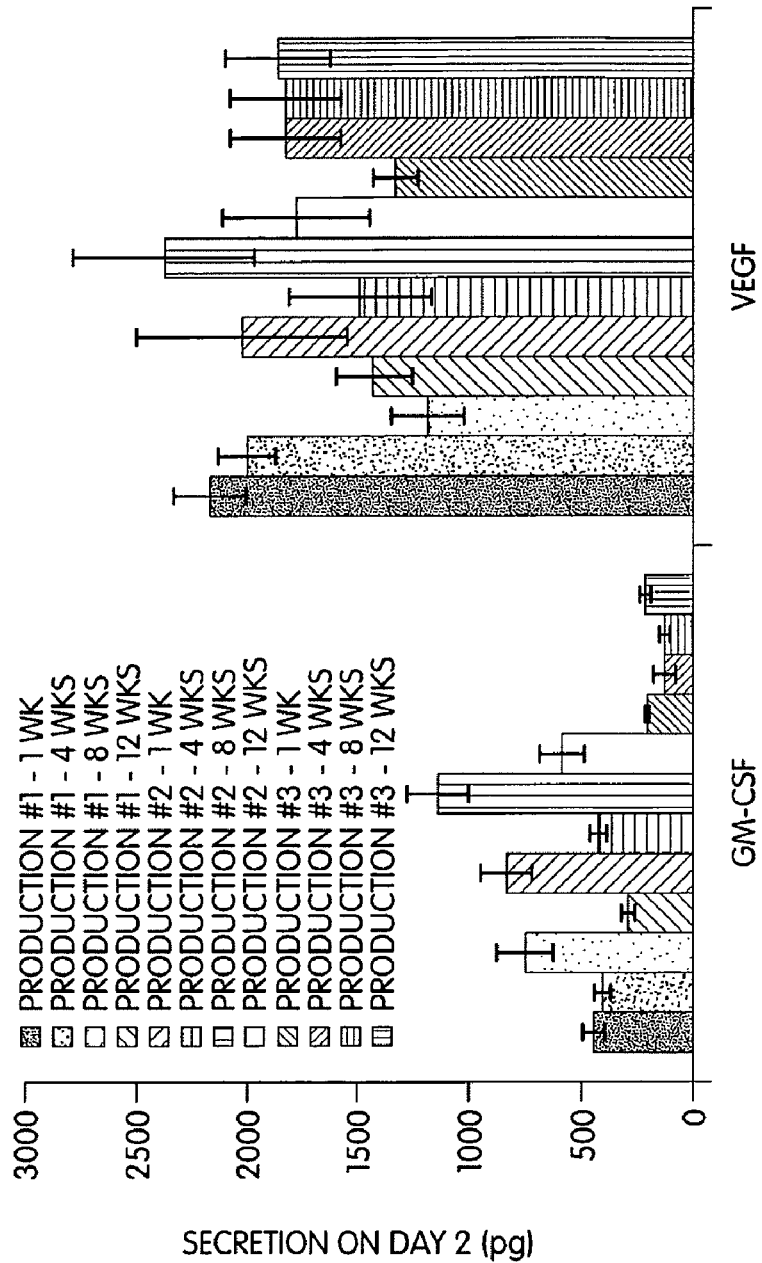
FIG. 10 is a histogram showing the secretion of the growth factors GM-CSF and VEGF by cell preparations manufactured at different productions following either one, four, eight, or twelve weeks of storage at −80° C. In this experiment, the cell preparation components were frozen using 15% glycerol+5% human serum albumin as the cryoprotectant.

FIG. 10 details the secretion of the human proteins GM-CSF and VEGF by cell preparations following storage at a temperature of −80° C. for extended periods. Data from three separate clinical production batches is shown. Batches containing a ratio of human primary fibroblasts to keratinocytes of 1:1 at a final concentration of $10 \times 10^6$ cells/ml were irradiated using gamma (γ) irradiation at 80Gy and frozen in a solution containing thrombin, 15% glycerol and 5% human serum albumin. Samples from each production batch were thawed following 1, 4, 8, and 12 weeks storage at −80° C. Thawed samples were subsequently sprayed into 24-well plates for testing. In individual wells, a single spray (130 μl) of cells+thrombin+cryoprotectant is mixed with a single spray (130 μl) of fibrinogen. The mixture of these two sprays creates a fibrin polymer matrix containing living fibroblasts and keratinocytes. The secretion of proteins by cells trapped in the fibrin matrix is measured during day 2 (the period lasting from 24 hours to 48 hours after thawing).

Secretion of GM-CSF and VEGF into the media by thawed cell preparations remains relatively stable over a period of storage lasting 3 months at −80° C. Slight variations in GM-CSF secretion was seen from individual batch to batch, though secretion within a batch appeared to be relatively stable. Secreted VEGF appeared stable, on average, both from a batch to batch perspective as well as within individual production batches. This data reveals that, with respect to GM-CSF and VEGF secretion, the product is stable in a cryogenic state at −80° C. for periods lasting at least 12 weeks. Data is presented as average±SEM.

Example 14

Comparison of Secretion after One Week Storage at −80° C. for Different Keratinocyte:Fibroblast Ratios FIG. 11 shows the secretion of growth factors from cryopreserved cell preparation formulations following one week of storage at −80° C. The graph shows differences in secretion for various human primary keratinocyte:fibroblast ratios, including 1:0, 1:1, and 1:9 as well as differences associated with total cell concentrations of 5, 10 and 20 million cells/ml. Prior to cryopreservation, cells were detached from their culture surfaces using trypsin and subsequently irradiated using gamma (γ) irradiation at 80Gy. A controlled rate freezer was used to gradually cool cell preparations to −80° C. After thawing one week later, one spray (130 μl) of the cell preparation (5, 10 and 20 million cells/ml) were spray mixed with one spray (130 μl) of fibrinogen in single wells of a 24 well petri dish.

A comparison of the secretion data for the 1:0 ratio and the 1:1 ratio showed the importance of adding fibroblasts to the keratinocytes in terms of GM-CSF and VEGF production. In all cases, there was a cell-dose dependant relationship with the secretion of the growth factors during the second day after thawing. The data also demonstrated that reducing the number of keratinocytes (i.e. by reducing the keratinocyte:fibroblast ratio to 1:9) did not lead to a reduction in overall growth factor secretion. These results were in accordance with the data obtained for "fresh" (non-frozen) cell preparations (see Example 9, supra) and suggested that only minimal quantities of keratinocytes were needed to produce the synergistic effect achieved by mixing the keratinocytes and fibroblasts together. This study also demonstrated that fibroblasts play an important role in the production of VEGF by cell preparations.

Example 15

Comparison of Growth Factor Secretion in Fresh and Cryopreserved Samples Stored at −80° C.

Prior to cryopreservation, cells were detached from their culture surfaces using trypsin and subsequently irradiated using gamma (γ) irradiation at 80Gy. Cell concentrations tested included 5, 10, and 20 million cells/ml (with a keratinocyte:fibroblast ratio 1:1), each mixed with 10% thrombin (Tisseel, Baxter) and the cryoprotectant. A controlled rate freezer was used to gradually cool cell preparations to −80° C. After thawing one week later, one spray (130 μl) of the cell preparation (5, 10 and 20 million cells/ml) were spray mixed with one spray (130 μl) of fibrinogen in single wells of a 24 well petri dish. To assess variability in frozen (cryopreserved) samples, 3 separate tubes for each condition were cryopreserved for one week at −80° C. Upon thawing, five samples were made per tube. The data presented in Table 8 is the average of the 15 samples available for each condition. The reproducible secretion data observed in the three frozen and thawed tubes per condition attests to the quality of the cryopreservation method. For fresh preparations, either 3 or 4 samples were made. Secretion of GM-CSF and VEGF by both freshly trypsinized and frozen cell preparations was observed to increase as cell density in the fibrin matrix increased from 2.5 to 5 to 10 million cells/ml (corresponding to 5, 10 and 20 million cells/ml found in original frozen preparations). This further illustrates the potential of dosing therapeutic effects by cell-based treatments.

TABLE 8

| Sample Name | Sample No. | GM-CSF (pg) | | | VEGF (pg) | | |
|---|---|---|---|---|---|---|---|
| | | Average | SEM | % Fresh | Average | SEM | % Fresh |
| 5 million/ml, Fresh | 4 | 40 | 14 | 100 | 1433 | 289 | 100 |
| 10 million/ml, Fresh | 4 | 270 | 128 | 100 | 3418 | 1293 | 100 |
| 20 million/ml, Fresh | 3 | 751 | 16 | 100 | 5628 | 1150 | 100 |
| 5 million/ml, 1 week at −80° C. | 15 | 81 | 11 | 202.5 | 986 | 96 | 68.8 |
| 10 million/ml, 1 week at −80° C. | 15 | 254 | 21 | 94.1 | 2135 | 254 | 62.5 |
| 20 million/ml, 1 week at −80° C. | 15 | 554 | 51 | 73.8 | 3462 | 335 | 61.5 |

Example 16

Evaluation of the Safety of the Frozen Cell Preparation of the Invention

The safety of the frozen wound-healing cell preparation of the invention has been evaluated in a multicenter, open phase I study. The cell preparation consisted of a kit containing two components. Component #1 was a suspension of fibrinogen and component #2 was a suspension of keratinocytes and fibroblasts mixed in thrombin and cryoprotectant. Cell preparations were frozen at −80° C., shipped to the clinic site at −80° C. and stored at −80° C. on site until use. Immediately prior to use, the cell preparation was thawed in a heated water bath. After thawing the two components (fibrinogen) and (cell+thrombin+cryoprotectants) were sequentially spray applied on the wound site, forming a thin fibrin matrix containing living keratinocytes and fibroblasts. Fourteen patients with chronic venous leg ulcers not responding to standard treatment with dressings and compression for at least 4-weeks (run-in phase) were enrolled in 5 centers in the Netherlands and Dutch Antilles. Ulcer sizes at baseline ranged from 0.3 to 20.4 cm2 (mean 5.8). Concomitant to the standard treatment, the cell preparation was then applied once weekly for up to 12 weeks or until complete closure, whichever came first.

No serious adverse events were reported in relation to this cell preparation. Four moderate to severe adverse events were thought to be attributable to the cell preparation (3×ulcer pain, 1× with increasing ulcer size). Moreover, there were no clinical signs of wound infection. Complete closure at week 12 was observed in 10 patients, 7 within 4 weeks and 3 within 4 to 12 weeks of treatment. Mean time to closure was 5.4 weeks.

In conclusion, the cell preparation of the invention is safe and well tolerated for the treatment of chronic venous leg ulcers.

Example 17

Spray Applied Living Keratinocytes and Fibroblasts as a Biologically Active Wound Dressing Primary fibroblasts and keratinocytes residing in the skin, naturally secrete a cocktail of growth factors and cytokines that act to stimulate the wound healing response following interruption of the cutaneous barrier. To mimic this natural process, a living cell-based wound dressing was developed for the treatment of chronic venous ulcers. It consists of two components: 1) a solution of fibrinogen; and 2) a suspension of keratinocytes and fibroblasts in thrombin and cryoprotectant. The product is stored frozen at −80° C. until use, at which time it is thawed, with the two components applied sequentially to the wound surface using a spray applicator. In this manner, polymerization of the fibrin occurs on the wound with delivered cells becoming trapped in a thin layer of fibrin at the ulcer site.

Mixtures of allogeneic, growth-arrested primary keratinocytes and fibroblasts were observed to secrete different levels of therapeutic proteins (VEGF, HGF, GM-CSF, bFGF, and KGF) depending on the ratios employed. Secretion of GM-CSF was dependant on the synergy derived from the mutual presence of fibroblasts and keratinocytes. Increasing the cell concentration in the final wound dressing from 1.25× $10^6$ cells/ml to $5 \times 10^6$ cells/ml led to an elevated secretion of growth factors and cytokines. Preliminary studies have shown that cell preparations remain biologically active for at least 2 months when stored at −80° C.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A kit comprising a container comprising:
   (a) a first component comprising:
      (i) fibrinogen;
      (ii) aprotinin; and
      (iii) a buffered solution,
   wherein the first component is comprised in a first sterile vial; and
   (b) a second component comprising:
      (i) fibroblasts;
      (ii) keratinocytes;
      (iii) thrombin;
      (iv) glycerol;
      (v) human serum albumin; and
      (vi) a buffered solution,
   wherein the second component is comprised in a second sterile vial.

2. The kit of claim 1, wherein the buffered solution in the first component is HBSS without $Ca^{++}$ and $Mg^{++}$ and the buffered solution in the second component is HBSS with $Ca^{++}$ and $Mg^{++}$.

3. The kit of claim 2, wherein the fibroblasts and keratinocytes are mitotically inactive.

4. The kit of claim 3, wherein the first and second components are cryopreserved.

5. The kit of claim 4, wherein the ratio of keratinocytes to fibroblasts is 1:9.

6. The kit of claim 5, wherein the container further comprises a first and a second removable lid, wherein the first removable lid is affixed to the first sterile vial and the second removable lid is affixed to the second sterile vial.

7. The kit of claim 6, wherein the kit further comprises spray pumps capable of replacing the removable lids.

8. The kit of claim 6, wherein the container further comprises a first and a second pouch, wherein the first sterile vial is comprised in the first pouch and the second sterile vial is comprised in the second pouch.

9. The kit of claim 8, wherein the first and second pouch is fabricated of a material capable of withstanding temperatures ranging from −80° C. to −160° C.

10. The kit of claim 9, wherein the container is an outer pouch or case.

* * * * *

UNITED STATES PATENT AND TRADEMARK OFFICE
CERTIFICATE OF CORRECTION

PATENT NO.        : 7,700,351 B2
APPLICATION NO.   : 12/255481
DATED             : April 20, 2010
INVENTOR(S)       : Eric Rolland et al.

It is certified that error appears in the above-identified patent and that said Letters Patent is hereby corrected as shown below:

In title page, item (73) Assignee, delete "DFB Pharmaceuticals, Inc." and insert
--DFB Technology Holdings, LLC-- therefor.

Signed and Sealed this

Twenty-sixth Day of October, 2010

David J. Kappos
*Director of the United States Patent and Trademark Office*